US010064556B2

(12) United States Patent
Umezawa

(10) Patent No.: US 10,064,556 B2
(45) Date of Patent: Sep. 4, 2018

(54) PHOTOACOUSTIC APPARATUS, SIGNAL PROCESSING METHOD OF PHOTOACOUSTIC APPARATUS, AND PROGRAM

(71) Applicant: CANON KABUSHIKI KAISHA, Tokyo (JP)

(72) Inventor: Kohtaro Umezawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 475 days.

(21) Appl. No.: 14/737,275

(22) Filed: Jun. 11, 2015

(65) Prior Publication Data
US 2015/0359434 A1 Dec. 17, 2015

(30) Foreign Application Priority Data
Jun. 13, 2014 (JP) ................. 2014-122535

(51) Int. Cl.
*A61B 5/05* (2006.01)
*A61B 5/00* (2006.01)
(Continued)

(52) U.S. Cl.
CPC ............ *A61B 5/0095* (2013.01); *A61B 5/145* (2013.01); *A61B 5/1455* (2013.01); *A61B 5/14542* (2013.01); *A61B 5/14546* (2013.01); *A61B 5/7207* (2013.01); *A61B 5/742* (2013.01); *A61B 5/748* (2013.01); *A61B 5/14532* (2013.01)

(58) Field of Classification Search
CPC ............................ A61B 19/5244; A61B 5/055
See application file for complete search history.

(56) References Cited

U.S. PATENT DOCUMENTS

2013/0044563 A1 2/2013 Watanabe et al.
2013/0286379 A1 10/2013 Li

FOREIGN PATENT DOCUMENTS

CN 101563035 B 8/2012
CN 102740765 A 10/2012
(Continued)

OTHER PUBLICATIONS

Sederberg et al., "Free-Form Deformation of Solid Geometric Models", SIGGRAPH, (1986), pp. 151-160, vol. 20, No. 4.
(Continued)

*Primary Examiner* — Hien Nguyen
(74) *Attorney, Agent, or Firm* — Canon USA Inc., IP Division

(57) ABSTRACT

A photoacoustic apparatus includes a light source generating multiple lights with different wavelengths, a converting element receiving photoacoustic waves generated in a subject by the subject being irradiated by the multiple lights, a first distribution obtaining unit obtaining a property distribution based on optical absorption within the subject, for each of the mutually different wavelengths, using time-sequence reception signals each output from the converting element for each of the mutually different wavelengths, a second distribution obtaining unit obtaining, using multiple property distributions based on optical absorption for each wavelength, a concentration-related distribution of a substance of an object region of the subject, and a statistical information obtaining unit obtaining statistical information indicating variance in distribution in at least part of the concentration-related distribution.

10 Claims, 12 Drawing Sheets

(51) Int. Cl.
A61B 5/145 (2006.01)
A61B 5/1455 (2006.01)

(56) References Cited

FOREIGN PATENT DOCUMENTS

| CN | 103356234 A | 10/2013 |
| CN | 103492871 A | 1/2014 |
| JP | 2010-512929 A | 4/2010 |
| WO | 2008075299 A1 | 6/2008 |
| WO | 2012137855 A1 | 10/2012 |

OTHER PUBLICATIONS

Zhang, et al., "Functional photoacoustic microscopy for high-resolution and noninvasive in vivo imaging", Nature Biotechnology, Jul. 2006, pp. 848-851, vol. 24, No. 7.

FIG. 6
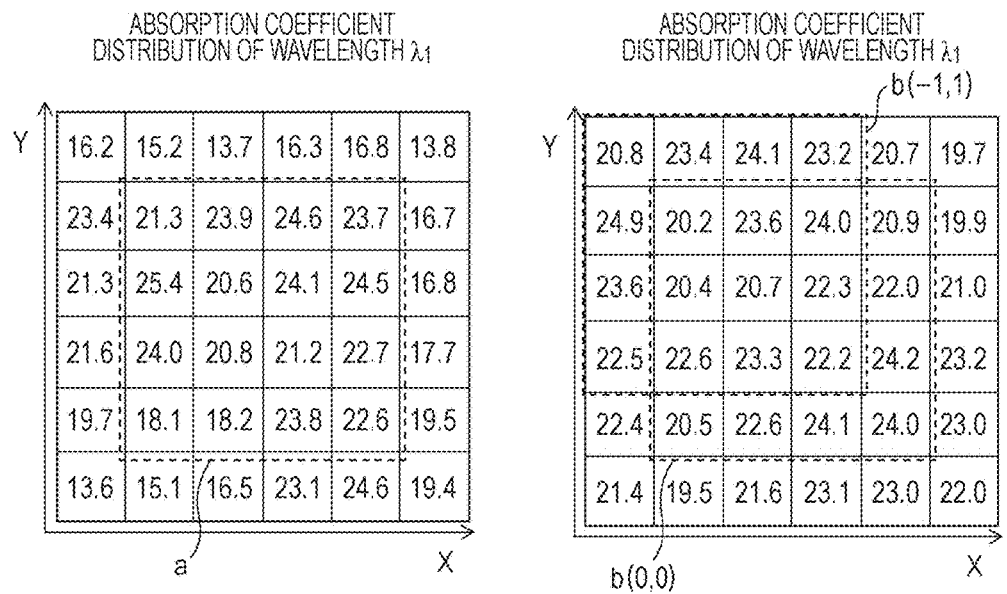
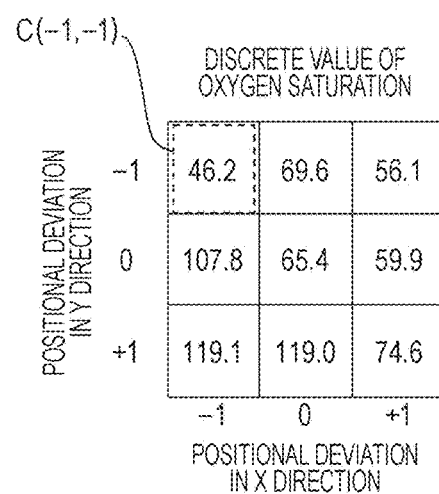

PHOTOACOUSTIC APPARATUS, SIGNAL PROCESSING METHOD OF PHOTOACOUSTIC APPARATUS, AND PROGRAM

BACKGROUND

Field

Aspects of the present invention generally relate to a photoacoustic apparatus for obtaining information of inside a subject, a signal processing method, and a program, and more particularly relates to technology using photoacoustic waves generated by a subject being irradiated by light.

Description of the Related Art

Research regarding imaging of functional information, which is physiological information of a living body, has come to be performed in the medical field in recent years. One technology in imaging of functional information is photoacoustic imaging (PAI).

In photoacoustic imaging, a subject is first irradiated by pulse light generated from a light source. The irradiation light propagates within the subject and diffuses. At multiple locations within the subject, energy of this light is absorbed, generating acoustic waves (hereinafter referred to as "photoacoustic waves"). The photoacoustic waves are received by converting elements, and the reception signals are analyzed and processed by a processor, thereby yielding distribution relating to optical property values within the subject as image data.

Distribution relating to optical property values are yielded in the form of sound pressure generated by optical absorption (initial sound pressure distribution), optical absorption coefficient distribution, and so forth. Also, irradiation using multiple pulse lights of different wavelengths and obtaining the optical absorption coefficients for each wavelength enables a concentration-related distribution of substances within the subject (a distribution of values relating to concentration of substances) to be obtained as a distribution relating to optical property values.

As for a concentration related distribution, there is the distribution of rate of content of oxyhemoglobin as to the total hemoglobin in the blood, i.e., blood oxygen saturation distribution. The optical absorption spectrums of deoxyhemoglobin and oxyhemoglobin are not the same. Accordingly, calculation of oxygen saturation uses the principle that the rate of content of each can be found by comparing the spectrums measured at different wavelengths, as disclosed in Hao F. Zhang, et al. "Functional photoacoustic microscopy for high-resolution and noninvasive in vivo imaging" Nature Biotechnology 24, 848-851 (July 2006).

At the time of performing tests by photoacoustic imaging, body movement occurs if the subject is a living body, due to breathing, pulse, actions, and so forth. When body movement occurs, positional deviation occurs between the initial sound pressure distributions calculated at different wavelengths, or between absorption coefficient distributions calculated at different wavelengths. Positional deviation among wavelengths can occur due to movement of a probe, in addition to body movement of the subject. The relatively positional deviation between the subject and the probe is a factor in lowering calculation accuracy of the oxygen saturation distribution.

PCT Japanese Translation Patent Publication No. 2010-512929 discloses detecting movement of tissue based on ultrasound images obtained by transmitting ultrasound waves and receiving the reflected waves, thereby estimating deformation of objects among the photoacoustic images.

The movement detection method disclosed in PCT Japanese Translation Patent Publication No. 2010-512929 is performed based on ultrasound images. Ultrasound images obtained by ultrasound echoes are distribution images reflecting difference in acoustic impedance, with structures where acoustic wave reflectance is great being visualized. On the other hand, structures where the rate of absorption is high are visualized in distributions regarding optical property values indicated by the photoacoustic image. Thus, the object of imaging is not the same in ultrasound images and photoacoustic images, so there is a possibility that reflecting movement detected based on ultrasound images in positional deviation among photoacoustic images may not be able to correct position deviation with high accuracy.

SUMMARY

A photoacoustic apparatus includes a light source configured to generate a plurality of lights with mutually different wavelengths, a converting element configured to receive photoacoustic waves generated in a subject by the subject being irradiated by the plurality of lights, a first distribution obtaining unit configured to obtain a property distribution based on optical absorption within the subject, for each of the mutually different wavelengths, using time-sequence reception signals output from the converting element for each of the mutually different wavelengths; a second distribution obtaining unit configured to, using a plurality of the property distributions based on optical absorption for each of the mutually different wavelengths, obtain a concentration-related distribution of a substance of an object region of the subject, and a statistical information obtaining unit configured to obtain statistical information indicating variance in distribution in at least a part of the concentration-related distribution. The second distribution obtaining unit obtains, based on the statistical information, a concentration-related distribution where positional deviation between the object region and the converting element at each of the mutually different wavelengths is suppressed.

Further features of the present disclosure will become apparent from the following description of exemplary embodiments with reference to the attached drawings.

BRIEF DESCRIPTION OF THE DRAWINGS

FIG. 6 is a schematic diagram for describing a method for deciding coordinate shift and positional deviation.

DESCRIPTION OF THE EMBODIMENTS

Figure 1:
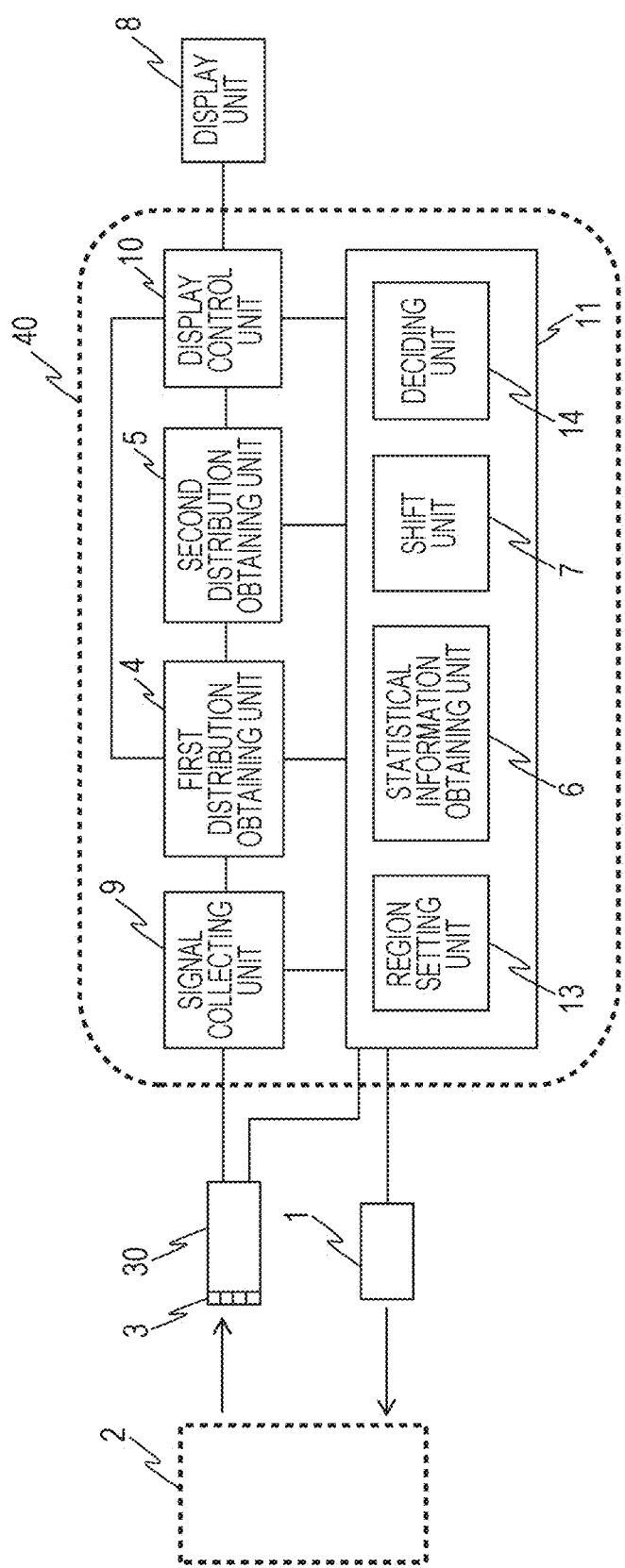
FIG. 1 is a schematic diagram illustrating the configuration of a photoacoustic apparatus according to an exemplary embodiment.

Exemplary embodiments will be described with reference to the drawings. Components that are the same will generally be denoted by the same reference numerals and description thereof omitted.

The photoacoustic apparatus according to an aspect of the present invention obtains information within a subject (information relating to optical property values) by using reception signals obtained by receiving photoacoustic waves. The term "photoacoustic waves" in the present Specification means acoustic waves generated by absorbing light, and includes so-called "acoustic waves", "ultrasound waves", "sound waves", "elastic waves", and "photo-ultrasound waves", generated by absorbing light.

Information relating to optical property values obtained in an aspect of the present invention reflects the rate of absorption of optical energy. Specific optical property values include "sound pressure (typically initial sound pressure)" of generated acoustic waves, "optical energy absorption density" derived from sound pressure, "absorption coefficients", "information relating to concentration (concentration-related information)" of a substance making up tissue, and so forth.

"Concentration-related information" includes values related to concentration of a substance present in the subject, that is obtained using "property distribution based on optical absorption" of multiple wavelengths. Specifically, "concentration-related information" is "oxygen saturation", "a value where oxygen saturation has been weighted by intensity of adsorption coefficients or the like", "total hemoglobin concentration", "oxyhemoglobin concentration", "deoxyhemoglobin concentration", and so forth. "Concentration-related information" may also be "glucose concentration", "collagen concentration", "melanin concentration", "volume fraction" of fat and water, and so forth.

The apparatus according to an aspect of the present invention can generate two-dimensional or three-dimensional distribution data, by obtaining optical property values at multiple positions. That is to say, "sound pressure distribution", "optical energy absorption density distribution", "absorption coefficient distribution", "concentration-related distribution", and so forth can be obtained. The obtained distribution data can be generated as image data.

Note that "sound pressure distribution", "optical energy absorption density distribution", and "absorption coefficient distribution" will be collectively referred to "property distribution based on optical absorption" in the present Specification. The "concentration-related distribution is obtained based on the "property distribution based on optical absorption" of multiple wavelengths.

The photoacoustic apparatus according to the following embodiments enables diagnosis of malignancy and blood vessel diseases in humans and animals, and for follow-up in chemotherapy. Accordingly, part of the living body that is the subject, more specifically one region of the human or animal (breast, body organs, circulatory organs, digestive system, bones, muscle, fat, etc.), is presumed to be the inspection target. Substances which are inspection targets include hemoglobin, glucose, water within the body, melanin, collagen, fat, and so forth. Further, radiopaque dye such as indocyanine green (ICG) administrated to the body may be the inspection target. It is sufficient that the inspection target has a characteristic optical absorption spectrum.

Exemplary embodiments will now be described. Note that the exemplary embodiments are not restricted to the photoacoustic apparatus itself, but also encompass a controlling method thereof, and a program for execution thereof.

First Embodiment

The following is a description of the configuration and processing thereof of a photoacoustic apparatus according to a first embodiment.

Overall Apparatus Configuration

FIG. 1 is a schematic diagram illustrating the configuration of the photoacoustic apparatus according to the present embodiment. The photoacoustic apparatus according to the present embodiment includes at least a light source 1, a probe 30 that has a converting element 3 which receives photoacoustic waves, and a signal processing unit 40 that performs signal processing using reception signals output from the converting element 3.

A subject 2 is irradiated by light output from the light source 1 and passing through an optical propagation member (omitted from illustration) such as fiber, lenses, and so forth. Note that the subject is irradiated by multiple pulse lights having different wavelengths from each other, at separate timings. The irradiation light propagates within the subject and diffuses, and is absorbed by substances present within the subject. Such substances which absorb light each absorb optical energy of each wavelength, and generate photoacoustic waves. That is to say, light of a first wavelength generates first photoacoustic waves, and light of a second wavelength generates second photoacoustic waves. The generated photoacoustic waves propagate through the subject and reach the converting element 3. The converting element 3 is provided so as to acoustically match the subject.

Each of multiple converting elements 3 output reception signals in time-sequence, by receiving the photoacoustic waves. That is to say, the converting elements 3 output first reception signals in time-sequence by receiving first photoacoustic waves, and output second reception signals in time-sequence by receiving second photoacoustic waves. The output reception signals are input to the signal processing unit 40. Reception signals are sequentially input to the signal processing unit 40, for each irradiated pulse light. The signal processing unit 40 generates distributions such as property distribution and concentration-related distribution, based on optical adsorption within the subject, using the input reception signals. The signal processing unit 40 also generates image data based on the generated distributions, and images can be displayed on a display unit 8. Input of region settings and so forth accepted from a user (operator such as a physician or technician) via an input unit 12.

In a case where the photoacoustic apparatus takes relatively small subjects as inspection targets, such as in a case of a photoacoustic microscope or the like, the number of converting elements 3 that the probe 30 has may be one. However, in a case where the photoacoustic apparatus takes a relatively large subject, such as a breast or the like, as the inspection target, multiple converting elements 3 are preferably provided to the probe 30.

Internal Configuration of Signal Processing Unit 40

Next, the configuration within the signal processing unit 40 according to the present embodiment will be described. The signal processing unit 40 according to the present embodiment has a signal collecting unit 9, a first distribution obtaining unit 4, a second distribution obtaining unit 5, a display control unit 10, and a control unit 11. The control unit 11 includes a region setting unit 13, a statistical information obtaining unit 6, a shift unit 7, and a deciding unit 14. The processing flow within the signal processing unit 40 will be described later with reference to FIG. 2, and the components within the signal processing unit 40 will be described first.

The signal collecting unit 9 collects time-sequence analog reception signals output from each of the multiple converting elements 3, by each channel, and performs signal processing such as amplifying the reception signals, AD conversion of the received analog signals, storage of digitized reception signals, and so forth.

The first distribution obtaining unit 4 generates property distributions based on optical absorption within the subject, using the reception signals output from the signal collecting unit 9. The following description relates to an example of obtaining absorption coefficient distribution as a property distribution based on optical absorption. An absorption coefficient $\mu_a$ at a position (i, j, k) within the subject can be obtained by Expression (1). Note that i, j, and k are each integers representing coordinates in the subject.

$$P = \Gamma \cdot \mu_a \cdot \phi \qquad (1)$$

where P represents initial sound pressure (generated sound pressure), $\Gamma$ represents the Grueneisen constant, and $\phi$ represents the quantity of light which has reached the position (i, j, k).

Note that the initial sound pressure at the position (i, j, k) on the three-dimensional spatial coordinates is obtained by image reconstruction, by filtering based on the reception signals for each channel that are output from the signal collecting unit 9, using a band correction filter of the probe. Examples of image reconstruction which may be used include known reconstruction techniques, such as universal back projection (UBP) described in U.S. Pat. No. 5,713,356, filtered back projection (FBP), and so forth. Delay-and-sum processing may also be used.

Performing this image reconstruction processing at each position obtains the initial sound pressure at each position, so the initial sound pressure distribution can be obtained. The initial sound pressure distribution may be three-dimensional distribution data (set data of voxels) corresponding to a certain region within the subject, or may be two-dimensional distribution data (set data of pixels) corresponding to one cross-section thereof.

Note that optical focusing photoacoustic microscopes, and acoustic focusing photoacoustic microscopes using focusing probes, can generate distribution data without performing image reconstruction processing. Specifically, the probe 30 and a light irradiation spot are moved relative to the subject 2 by a scanning mechanism (omitted from illustration), and the probe 30 receives photoacoustic waves at multiple scanning positions. After having performed envelope detection regarding time change of the obtained reception signals, the first distribution obtaining unit 4 performs conversion of the temporal axis direction of the signals in each optical pulse into the depth direction, and plots this on spatial coordinates. Distribution data can be configured by performing this at every scan position.

The first distribution obtaining unit 4 obtains the absorption coefficient distribution using Expression (1), based on the initial sound pressure obtained in this way. Note that the Grueneisen constant can be considered to be constant. The light quantity $\phi$ may be considered to be constant in the subject, but the light quantity distribution is preferably obtained by performing calculation taking into consideration optical propagation within the subject, from the light quantity distribution input to the subject, in order to obtain concentration-related information more accurately. Accordingly, the first distribution obtaining unit 4 obtains the absorption coefficient distribution using the initial sound pressure and the light quantity distribution. Thus, the first distribution obtaining unit 4 according to the present embodiment obtains the absorption coefficient distribution for each of the multiple wavelengths emitted from the light source 1, and outputs to the second distribution obtaining unit 5.

The second distribution obtaining unit 5 uses multiple absorption coefficient distributions for each wavelength output from the first distribution obtaining unit 4, and generates concentration-related distribution. An example of obtaining oxygen saturation distribution as the concentration-related distribution will be described below.

Assuming that optical absorption other than due to hemoglobin is negligible at wavelength $\lambda_1$ and wavelength $\lambda_2$, the absorption coefficients for wavelength $\lambda_1$ and wavelength $\lambda_2$ are each expressed as in Expressions (2) and (3), using the molar absorption coefficient for oxyhemoglobin and the molar absorption coefficient for deoxyhemoglobin.

$$\mu_a(\lambda_1) = \varepsilon_{ox}(\lambda_1)C_{ox} + \varepsilon_{de}(\lambda_1)C_{de} \qquad (2)$$

$$\mu_a(\lambda_2) = \varepsilon_{ox}(\lambda_2)C_{ox} + \varepsilon_{de}(\lambda_2)C_{de} \qquad (3)$$

In these Expressions, $\mu_a(\lambda_1)$ represents the absorption coefficient of light of the wavelength $\lambda_1$ at position (i, j, k), $\mu_a(\lambda_2)$ represents the absorption coefficient of light of the wavelength $\lambda_2$ at position (i, j, k), in units of $mm^{-1}$. $C_{ox}$ is the amount of oxyhemoglobin in mols, and $C_{de}$ is the amount of deoxyhemoglobin in mols. Each represent values at position (i, j, k).

$\varepsilon_{ox}(\lambda_1)$ and $\varepsilon_{de}(\lambda_1)$ represent the molar absorption coefficient ($mm^{-1}mol^{-1}$) of oxyhemoglobin and deoxyhemoglobin at wavelength $\lambda_1$, respectively, and $\varepsilon_{ox}(\lambda_2)$ and $\varepsilon_{de}(\lambda_2)$ represent the molar absorption coefficient ($mm^{-1}mol^{-1}$) of oxyhemoglobin and deoxyhemoglobin at wavelength $\lambda_2$, respectively. $\varepsilon_{ox}(\lambda_1)$, $\varepsilon_{de}(\lambda_1)$, $\varepsilon_{ox}(\lambda_2)$, and $\varepsilon_{de}(\lambda_2)$ can be found beforehand by measurement or literature values.

Accordingly, $C_{ox}$ and $C_{de}$ are each obtained using the molar absorption coefficient, $\mu_a(\lambda_1)$, and $\mu_a(\lambda_2)$, by solving the simultaneous equations in Expressions (2) and (3). In a case where the number of wavelengths used is great, the least square method is preferably used. The oxygen saturation $SO_2$ is defined as the rate of oxyhemoglobin in total hemoglobin, as shown in Expression (4). Accordingly, the oxygen saturation $SO_2$ can be shown by Expression (5), based on Expressions (2), (3), and (4).

Thus, the second distribution obtaining unit 5 can obtain the oxygen saturation $SO_2$ at position (i, j, k) based on the molar absorption coefficient, $\mu_a(\lambda_1)$, and $\mu_a(\lambda_2)$, using the Expression (5).

$$SO_2 = \frac{C_{ox}}{C_{ox} + C_{de}} \quad (4)$$

$$SO_2 = \frac{\frac{\mu_a(\lambda_2)}{\mu_a(\lambda_1)} \cdot \varepsilon_{de}(\lambda_1) - \varepsilon_{de}(\lambda_2)}{(\varepsilon_{ox}(\lambda_2) - \varepsilon_{de}(\lambda_2)) - \frac{\mu_a(\lambda_2)}{\mu_a(\lambda_1)} \cdot (\varepsilon_{ox}(\lambda_1) - \varepsilon_{de}(\lambda_1))} \quad (5)$$

Figure 3:
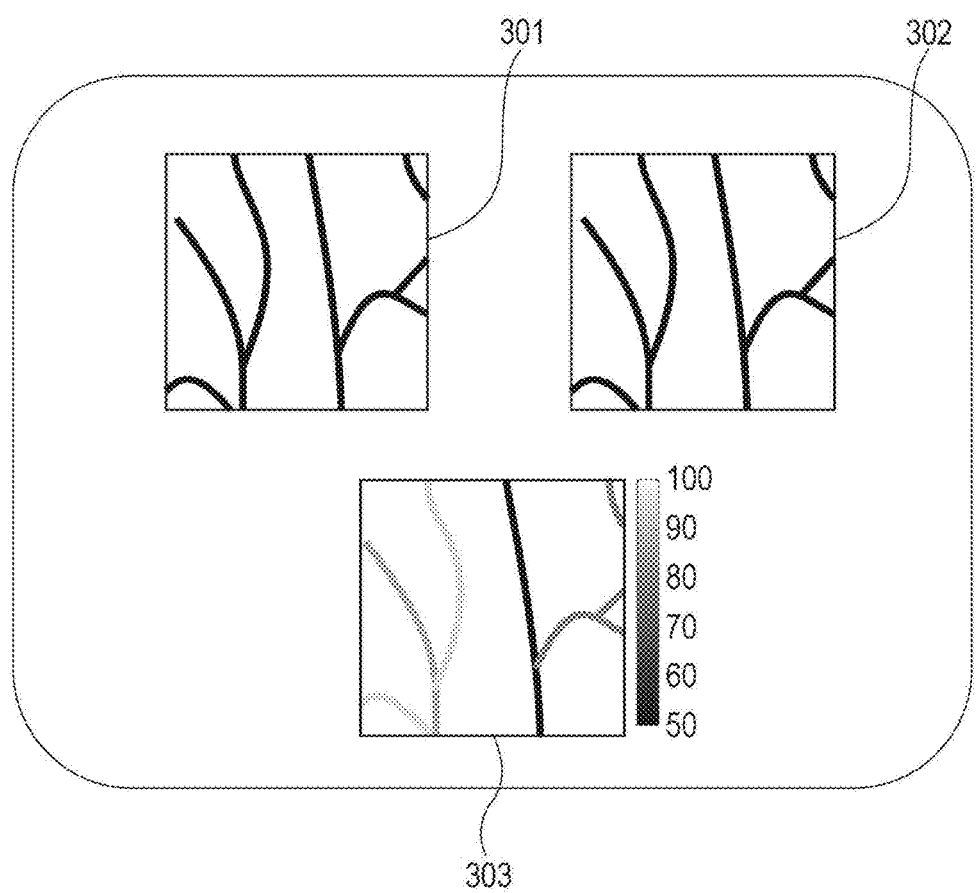
FIG. 3 is a schematic diagram illustrating an example of a display image according to an exemplary embodiment.

Performing such processing at each position yields the oxygen saturation at each position, so an oxygen saturation distribution can be obtained. FIG. 3 illustrates an example of a display screen where an oxygen saturation distribution has been obtained from the absorption coefficient distribution of wavelength $\lambda_1$ and the absorption coefficient distribution of wavelength $\lambda_2$. Reference numeral 301 denotes the oxygen saturation distribution at wavelength $\lambda_1$, reference numeral 302 denotes the oxygen saturation distribution at wavelength $\lambda_2$, and reference numeral 303 denotes an image of the oxygen saturation distribution. The oxygen saturation distribution may be three-dimensional distribution data (set data of voxels) corresponding to a certain region within the subject, or may be two-dimensional distribution data (set data of pixels) corresponding to one cross-section thereof.

The statistical information obtaining unit 6 obtains statistical information indicating variance in at least part of the distribution in the oxygen saturation distribution obtained by the second distribution obtaining unit 5. It is sufficient for the statistical information indicating variance to be an evaluation index indicating variance in value within a distribution (particularly variance from a center value (typically an average value)), such as dispersion value, standard deviation, half value of histogram, entropy (average information amount of pixel values), and so forth. Also, in a case of an evaluation index where the larger the value is, the smaller the variance is, calculation processing may be performed such as integration of the evaluation index by −1, so that the evaluation index is read as having smaller variance the smaller the value is. A specific way of obtaining statistical information will be described later with reference to FIG. 4.

The positional deviation between the absorption coefficient distributions obtained for each wavelength (i.e., the positional deviation between the probe and subject at each wavelength) can be estimated by this statistical information in the present embodiment. Specifically, in a case where this statistical information (e.g., dispersion value) is small, the positional deviation among wavelengths can be determined to be small, and if the statistical information is large, and the positional deviation among wavelengths is large. Note that "positional deviation between probe and subject" includes "positional deviation between probe and partial region within subject".

The reason why positional deviation can be determined from statistical information indicating dispersion in oxygen saturation distribution in this way will be described. Generally, the oxygen saturation value of blood in blood vessels differ at micro-level viewpoints such as at blood cells or clusters thereof. However, when observing blood cells (10 μm or smaller) in blood vessels with a device having spatial resolution of several hundred μm to several mm (in a range of 100 μm to 10 mm), the oxygen saturation of blood cells and clusters appear to be spatially averaged. Also, even when using a device having high spatial resolution (10 μm or smaller) but with poor temporal resolution, the oxygen saturation of blood cells and clusters appear to be spatially averaged. That is to say, when the device being used has spatial resolution or temporal resolution such that the oxygen saturation of individual blood cells cannot be distinguished, the oxygen saturation of blood in the blood vessels becomes an averaged value.

This is generally true for large blood vessels around several hundred μm to several mm, but is not restricted to this, and the same can be conceived to be true at blood vessel portions where there is no tissue other than blood vessel partway along the blood vessel and blood reflux speed is fast. This sort of phenomenon is thought to occur regardless of differences between arteries and veins.

Accordingly, if there is no deviation between absorption coefficient distributions, and the oxygen saturation distribution has been correctly found, the value of statistical information such as the dispersion value of oxygen saturation distribution will be contained in a relatively small value. Accordingly, in a case where the statistical information representing dispersion assume a large value, it is conceivable that variance within the oxygen saturation distribution is large, due to deviation among the absorption coefficient distributions.

The region setting unit 13 can set an object region to obtain an oxygen saturation distribution within an absorption coefficient distribution, set a target region for obtaining statistical information within an oxygen saturation distribution, or the like. That is to say, the oxygen saturation distribution in the present embodiment may be obtained for a partial region within the absorption coefficient distribution, and is not restricted to cases of the same range as the absorption coefficient distribution. The region setting unit 13 further may set a target region for further obtaining statistical information with regard to an oxygen saturation distribution within the object region obtained by the second distribution obtaining unit 5. This is because there is no need to use oxygen saturation distribution at locations other than blood as statistical information.

As for a method for the region setting unit 13 to set object regions and target regions, there is a method of performing settings based on region information which the user has input using the input unit 12. There is also a method where the region setting unit 13 performs settings automatically, based on the intensity within the initial sound pressure distribution or absorption coefficient distribution. Either a two-dimensional region or a three-dimensional region may be set. The shape of the region being set may be a shape matching the structural part, or a cuboid, or any shape.

As for a method where the region is set based on user input, there is a method where the region setting unit 13 sets the region based on a region which the user has set on the image using the input unit 12 while viewing a display screen such as shown in FIG. 3. For example, in a case of setting an object region, the user selects (surrounds as a setting range) part or all of a structural part conceivably a blood vessel, on an image from one of the absorption coefficient distributions of $\lambda_1$ and $\lambda_2$. The region setting unit 13 may set this setting range as an object range for obtaining the oxygen saturation distribution. Further, a target range may be set by the user selecting a partial region on the image of the oxygen saturation distribution. The region setting unit 13 preferably performs this setting by surrounding a region two-dimensionally if the distribution is two-dimensional, and three-dimensionally if the distribution is three-dimensional.

In a case where the region setting unit 13 automatically sets the region, first, processing is performed to extract an object region such as a blood vessel or the like in a region in the same range as the absorption coefficient distribution, and thereafter at least a part of the region within the object region is preferably set as a target region. As for a method of setting the object region, there is a method of extracting a portion where the intensity is higher than a predetermined value (threshold value) in the absorption coefficient distribution, and so forth. There are also other methods which may be used, such as a method of performing template matching processing using an image template unique to the object structure part, or methods of extracting by performing image processing using snakes, Level Set, or the like. If the S/N ratio of the object structure part portion is high in the distribution, the entire structure body does not have to be extracted. As for a method for setting the target region, scanning can be performed from the edge of the oxygen saturation distribution within the object region set earlier, and labeling processing performed on portions where the structure part is found to exist as a single continuation, thereby setting the target region.

The shift unit 7 performs coordinate shift processing for relatively shifting the coordinates among the absorption coefficient distributions used for oxygen saturation distribution calculation, for the second distribution obtaining unit 5. This coordinate shift processing can be performed by copying the absorption coefficient distribution within the set target region, and replacing with the absorption coefficient distribution at the shift destination. Note however, that alpha blending with the absorption coefficient distribution at the shift destination may be performed at a suitable rate. Alternatively, affine transform, or non-rigid transform or the like by performing optimization calculation of statistical information as evaluation functions, may be performed instead of replacing distributions or performing alpha blending. At the time of performing optimization calculation, a gradient algorithm may be used such as in method of steepest descent or conjugate gradient method. The specific shift method will be described later with reference to FIG. 6. The shift unit 7 performs this relative coordinate shift processing several times. The second distribution obtaining unit 5 obtains the oxygen saturation distribution for each shift, and the statistical information obtaining unit 6 obtains statistical information for the target region for each oxygen saturation distribution obtained. That is to say, the second distribution obtaining unit 5 obtains the concentration-related distribution within the target region multiple times for multiple times of coordinate shift processing, and the statistical information obtaining unit 6 obtains a plurality of statistical information.

The deciding unit 14 decides the amount of positional deviation, based on the multiple statistical information obtained by multiple times of coordinate shift processing. For example, the vector in coordinate shift in a case where the dispersion value of the oxygen saturation distribution within the target region is smallest is decided to be the positional deviation among absorption coefficient distributions. That is to say, the absorption coefficient distributions in relative positional relation in a case where the dispersion value is the smallest, becomes the absorption coefficient distributions after correction of positional deviation. A specific deciding method will be described later with reference to FIG. 6.

It should be noted, however, that positional deviation may be decided by the deciding unit 14 based on coordinate shift in a case where the statistical information is smaller than a predetermined value, and not just a case of the statistical information being the smallest value. That is to say, even if not the smallest value, of a value which can be tolerated as variation is set as a threshold value and the statistical information is smaller than that threshold value, the vector of coordinate shift at that time can be decided as the positional deviation. Such settings also enable oxygen saturation distributions with suppressed (reduced) effects of positional deviation to be obtained.

In a case where the statistical information is smaller than statistical information in a case with no coordinate shift, out of the multiple statistical information, the relative positional relation between the absorption coefficient distributions is in a state where positional deviation has been suppressed (reduced). Accordingly, the predetermined value may be a statistical information value in a case of no performing coordinate shifting. In the present embodiment, it is sufficient if positional deviation is suppressed, even if not completely corrected. That is to say, even if the effects of positional deviation are not completely eradicated by coordinate shifting, an advantage can be obtained that oxygen saturation distribution with higher accuracy than the related art can be obtained as long as the effects of positional deviation are reduced.

The display control unit 10 generates image data of displaying on the display unit 8, based on the distribution data such as the absorption coefficient distribution generated by the first distribution obtaining unit 4 and the oxygen saturation distribution generated by the second distribution obtaining unit 5. Specifically, image processing such as luminance conversion, distortion correction, logarithmic compression, and so forth, is performed based on the distribution data. Further, display control is performed such as arraying various types of display items along with the distribution data, updating the display based on instructions from the input unit 12, and so forth.

The control unit 11 has the region setting unit 13, statistical information obtaining unit 6, shift unit 7, and the deciding unit 14, and also supplies control signals and data necessary for the configuration blocks within the photoacoustic apparatus, to control these configuration blocks. Specifically, the control unit 11 supplies signals instructing the light source 1 to emit light, and control signals to the converting elements 3 within the probe 30. The control unit 11 also controls signal amplifying at the signal collecting unit 9, control of AD conversion timing, control of storage of received signals, and so forth. The control unit 11 also transmits control signals related to distribution data generation to the first and second distribution obtaining units, and reception of distribution data. The control unit 11 also transmits control signals relating to image generating to the display control unit 10, and receives image data from the display control unit 10. The control unit 11 further is connected to the input unit 12 for the user to input various types of operations and instructions, and accepts input information from the user via the input unit 12. In a case of moving the probe 30, the control unit 11 may perform moving control. Moreover, the control unit 11 may hold reception signals, generated distribution data, display image data, various types of measurement parameters, and so forth.

Processing Flow at Signal Processing Unit 40

Figure 2:
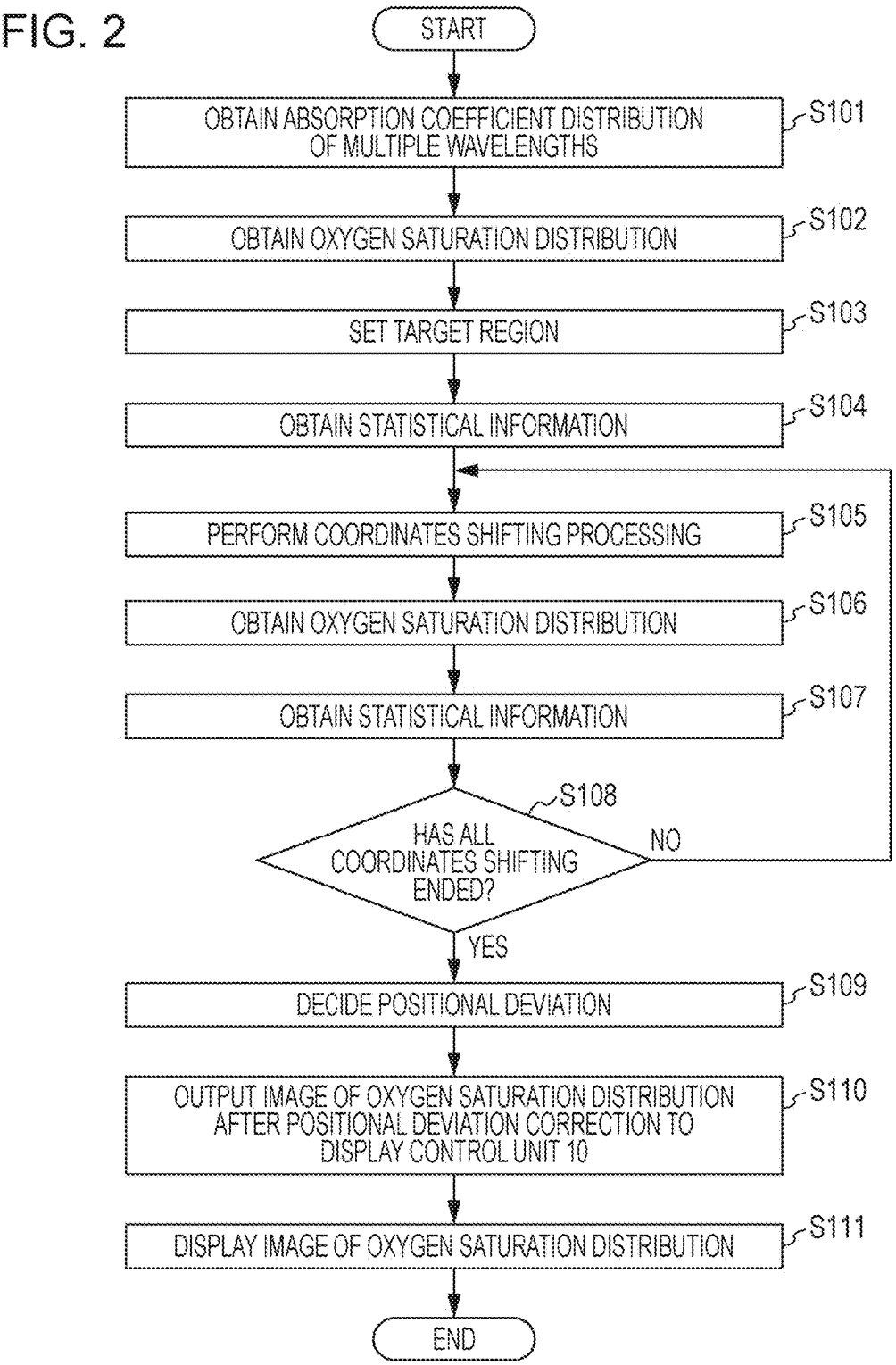
FIG. 2 is a flowchart illustrating operations of a signal processing unit according to an exemplary embodiment.

Next, the processing flow at the signal processing unit 40 will be descried. FIG. 2 is a flowchart illustrating the processing flow at the signal processing unit 40 according to the present embodiment. Note that the flow in FIG. 2 starts from a state where reception signals are sequentially input to the signal collecting unit 9 within the signal processing unit 40 from the probe, for each wavelength of the irradiation light, and processing such as AD conversion and amplifying and so forth has been performed at the signal collecting unit 9.

In step S101, the first distribution obtaining unit 4 obtains the absorption coefficient distribution at the wavelength $\lambda_1$ using reception signals of light with the wavelength $\lambda_1$, and obtains the absorption coefficient distribution at the wavelength $\lambda_2$ using reception signals of light with the wavelength $\lambda_2$.

In step S102, the second distribution obtaining unit 5 generates oxygen saturation distribution within the object region using the absorption coefficient distribution at wavelength $\lambda_1$ and the absorption coefficient distribution at wavelength $\lambda_2$. Note that the object region may be a partial region within the absorption coefficient distribution set by the region setting unit 13, or the object region may be the same range as the range of the absorption coefficient distribution.

In step S103, the region setting unit 13 sets at least part of the oxygen saturation distribution obtained by the second distribution obtaining unit 5 as the target region. Here, an example will be described in which the target region is set based on user input. In this case, the display control unit 10 generates image data based on data of the oxygen saturation distribution obtained by the second distribution obtaining unit 5. The display control unit 10 displays an image of oxygen saturation distribution such as illustrated in FIG. 3, on the display unit 8. Upon the user using the input unit 12 to instruct a predetermined region on the image of the displayed oxygen saturation distribution, the region setting unit 13 sets the specified region as the target region.

In step S104, the statistical information obtaining unit 6 obtains statistical information indicating the variance in the oxygen saturation distribution within the target region. An example of obtaining dispersion as statistical information will be described. Dispersion can be expressed as in the following Expression (6).

$$\sigma^2 = \frac{1}{m}\sum_{i=1}^{m}(M - x_i)^2 \qquad (6)$$

When M represents the average value of a population of m pieces of data ($x_1$ through $x_m$), the arithmetic mean $\sigma^2$ represents dispersion in Expression (6). Note that in the present embodiment, $x_i$ corresponds to each voxel value (or pixel value), and M corresponds to the average value thereof.

Figure 4:
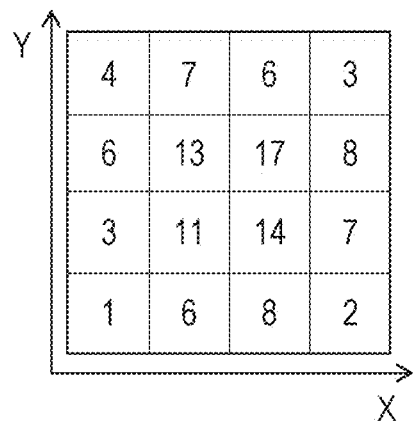
FIG. 4 is a schematic diagram for describing a way to obtain dispersion.

Description will be made in further detail with reference to FIG. 4. FIG. 4 is a schematic diagram illustrating 4×4 distribution for a target region. Note that the Z axis is not drawn in FIG. 4 for the sake of simplicity, and only the X-Y coordinates are shown for description. The values described in each voxel in FIG. 4 represent the intensity of that voxel. Here, the average value M=(total of elements)/16=7.25, and the dispersion value $\sigma^2 = \Sigma(\text{elements}-7.25)^2/16=19.19$. The dispersion value obtaining in this way is saved in memory in the control unit 11.

In step S105, the shift unit 7 performs processing for relative positional shifting of the absorption coefficient distribution at wavelength $\lambda_1$, and the absorption coefficient distribution at wavelength $\lambda_2$. FIG. 6 is a schematic diagram for describing a method for obtaining coordinate shift and dispersion. In FIG. 6, the distribution at the left side represents the absorption coefficient distribution at wavelength $\lambda_1$, the distribution at the right side represents the absorption coefficient distribution at wavelength $\lambda_2$, both being represented as a set of 6×6 voxels. Note that the Z axis is not drawn here for the sake of simplicity, and only the X-Y coordinates are shown for description. The values described in each voxel represent the intensity of that voxel (value of absorption coefficient in this case).

Now, the position of a 4×4 distribution "a" at the center of the absorption coefficient distribution for the wavelength $\lambda_1$ represents the region set as the target region in S103. The shift unit 7 performs parallel movement of the absorption coefficient distribution at wavelength $\lambda_2$ in one of the depth, width, and height directions (X, Y, Z directions) by one voxel at a time (by one coordinate at a time), with the absorption coefficient distribution of the target region of this wavelength $\lambda_1$ as a reference.

FIG. 6 illustrates a distribution moved −1 in the X direction and +1 in the Y direction from a reference position, which is a distribution b(0, 0) of wavelength $\lambda_2$ at the same position as the target region (distribution "a") of the wavelength $\lambda_1$, as b(−1, 1). Shifting −1 and +1 each in the X and Y directions gives a total of nine patterns for coordinate shifting.

In step S106, the second distribution obtaining unit 5 obtains the oxygen saturation distribution of the target region, using the absorption coefficient distributions of the wavelength $\lambda_1$ and wavelength $\lambda_2$ relatively coordinate-shifted. For example, FIG. 6 yields the oxygen saturation distribution using the target region of the wavelength $\lambda_1$ (distribution "a") and the distribution b(−1, 1) of the wavelength $\lambda_2$ after coordinate shifting.

In step S107, the statistical information obtaining unit 6 obtains statistical information representing variance of oxygen saturation distribution within the target region obtained in S106. The distribution of dispersion, which is the statistical information, is illustrated at the bottom of FIG. 6. For example, the dispersion of the oxygen saturation distribution obtained using the target region of the wavelength $\lambda_1$ (distribution "a") and the distribution b(−1, 1) of the wavelength $\lambda_2$ after coordinate shifting is shown as dispersion c(−1, −1). The dispersion value obtained as statistical information in this step is saved in memory in the control unit 11, in the same way as in S104.

In step S108, the control unit 11 determines whether the coordinate shifting by the shift unit 7 has all ended. For example, upon all nine patterns, described above regarding FIG. 6, of the coordinate shifting ending, determination is made that the coordinate shifting has ended. Generally, in a case of an apparatus which receives photoacoustic waves in a still state, the amount of positional deviation that occurs is within 2 mm or so. Accordingly, in a case of moving in parallel a maximum of 8 voxels in the X direction, Y direction, and Z direction, the number of coordinate shift patterns is 4,913. In detail, there are 8+1+8=17 combinations in the X direction (8 in the positive direction, 1 not shifting (staying at X=0), and 8 in the negative direction). The Y coordinates and Z coordinate also have these combinations, so the total number of combination patterns for coordinate shifting is (8+1+8)×(8+1+8)×(8+1+8)=4,913 patterns.

Thus, upon all of the combination patterns set beforehand ending, the coordinate shifting is determined to have ended. In a case where the coordinate shifting is determined to have ended, the flow advances to S109, and if the coordinate shifting has not ended, the flow returns to S105.

Thus, repeating S105 through S108 obtains multiple oxygen saturation distributions based on the target region of wavelength $\lambda_1$ (distribution "a") and the distribution b(i, j) of the wavelength $\lambda_2$. Further, dispersion corresponding to each of the multiple oxygen saturation distributions is also obtained.

In S109, the deciding unit 14 decides the positional deviation between the probe and the subject, based on the plurality of statistical information calculated in S104 and S107. The coordinate shift where the dispersion is the smallest out of the multiple dispersions is decided as the positional deviation between the absorption coefficient distributions (relative positional deviation between the absorption coefficient distribution of the wavelength $\lambda_1$ and the absorption coefficient distribution of the wavelength $\lambda_2$). The reason is that the smallest value for dispersion can be though to mean that the variance within the obtained oxygen saturation distribution is the smallest.

That is to say, the vector of the coordinate shift where the dispersion is the smallest value corresponds to the relative positional deviation between the probe and the subject. In other words, the relative positional relation between the absorption coefficient distributions when the dispersion is the smallest is the absorption coefficient distributions with each other after positional deviation correction. Of the nine patterns of coordinate shift in FIG. 6, the dispersion (represented by c(−1, −1)) at the time of coordinate shift represented by distribution b(−1, 1) of wavelength $\lambda_2$ is the smallest dispersion. The deciding unit 14 transmits the vector of the coordinate shift thus decided (information relating to the positional deviation) to the second distribution obtaining unit 5.

In S110, the second distribution obtaining unit 5 outputs oxygen saturation distribution data obtained using the absorption coefficient distributions after positional deviation correction to the display control unit 10, based on information relating to positional deviation from the deciding unit 14. Note that oxygen saturation distribution is obtained for the multiple times of coordinate shifting, so the second distribution obtaining unit 5 can read out the oxygen saturation distributions from the memory and transmit to the display control unit 10, if the oxygen saturation distributions have been saved in the memory in the control unit 11. The second distribution obtaining unit 5 may newly obtain an oxygen saturation distribution using the absorption coefficient distributions following positional deviation correction.

In S111, the display control unit 10 generates image data based on the oxygen saturation distribution data output from the second distribution obtaining unit 5, and displays on the display unit 8.

Thus, according to the present embodiment, positional deviation is obtained based on oxygen saturation distributions for imaging, so more accurate positional deviation detection can be realized, and oxygen saturation distribution can be obtained with higher accuracy.

Note that the second distribution obtaining unit 5 in the above-described example obtains oxygen saturation distribution as the concentration-related distribution, but the present embodiment is not restricted to this. As described earlier, "distribution of values relating to concentration of substance (concentration-related distribution) obtained using "property distribution based on optical absorption" of multiple wavelengths, suffices. That is to say, distributions such as "weighed oxygen saturation value", "total hemoglobin concentration", "oxyhemoglobin concentration", "deoxyhemoglobin concentration", "glucose concentration", "collagen concentration", "melanin concentration", "volume fraction" of fat and water, and so forth are all acceptable.

The first distribution obtaining unit 4 has been described in the above example as obtaining absorption coefficient distributions as property distributions based on optical absorption, but the present embodiment is not restricted to this, and may use "sound pressure distribution (typically initial sound pressure distribution)" or "optical energy absorption density distribution". For example, since $\mu_a$ can be expressed as $P/(\Gamma \cdot \phi)$ from Expression (1), substituting $P/(\Gamma \cdot \phi)$ for $\mu_a$ in Expression (5) enables the oxygen saturation distribution to be directly obtained from the initial sound pressure. That is to say, the second distribution obtaining unit 5 can directly obtain the oxygen saturation distribution from the initial sound pressure distribution data, without the first distribution acquiring unit 4 having to go through the process of obtaining absorption coefficient distribution after obtaining the initial sound pressure distribution.

Also, while an example has been described above where the structure body serving as the object region is the blood portion within blood vessels, the present embodiment is not restricted to this. Blood vessel walls, lymph ducts, muscle tissue, mammary gland tissue, fat tissue, and aggregations of substances externally injected such as a molecular target drug serving as a radiopaque dye, may be used. The object region is preferably selected according to the substance regarding which the concentration is to be obtained.

Specific configuration examples of the components of the present embodiment will be described next.

Light Source 1

The light source 1 preferably is a pulsed light source capable of emitting pulsed light of pulses in the nanosecond to microsecond order. The specific pulse width used is in the range of around 1 nanosecond to 100 nanoseconds. The wavelength used is in the range of 400 nm to 1600 nm. Particularly, in cases of imaging deep portions of a living body, light of a wavelength band referred to as a "biological window" due to low absorption by background tissue of the body is used. Specifically, light of a wavelength range of 700 nm to 1100 nm is preferable. On the other hand, the visible light region is preferably used when imaging blood vessels near the surface of the body at high resolution. However, terahertz waves, microwaves, and radio wave regions may also be used.

Specifically, laser is preferably for the light source 1, and laser with variable oscillation wavelength is preferable since the present embodiment uses light of multiple wavelengths. However, an arrangement may be made wherein multiple laser devices with different oscillation wavelengths are used, switching oscillation from one to another, since it is sufficient to be able to irradiate the subject with multiple wavelengths. Also, an arrangement may be made wherein multiple laser devices with different oscillation wavelengths are used, switching emission from one to another. Arrangements where multiple laser devices are used will also be collectively referred to as "light source".

Examples of lasers which can be used include solid-state laser, gas laser, dye laser, semiconductor laser, and so forth. Particularly preferable are pulsed lasers such as neodymium-doped yttrium aluminum garnet (Nd:YAG) laser and alexandrite laser. Also usable are titanium sapphire (Ti:sa) laser which uses Nd:YAG laser light as excitation light, and optical parametric oscillator (OPO) laser. Light-emitting diodes or the like may also be used instead of laser.

The pulsed laser output from the light source is preferably guided to the subject by members which propagate light (optical members), such as optical fiber, lenses, mirrors, diffusing plates, and so forth. The spot shape and beam density of the pulsed light can be changed using such optical members when guiding the pulsed light.

Probe 30

The probe 30 has one or more converting elements 3. Any sort of converting element may be used for the converting elements 3 as long as photoacoustic waves can be received and converted into electric signals, examples including piezoelectric elements using the piezoelectric phenomenon, such as lead zirconate titanate (PZT), converting elements using light resonance, electrostatic capacitance type converting elements such as capacitive micromachined ultrasonic transducers (CMUT), and so forth. In a case of having multiple converting elements 3, the converting elements 3 are preferably arrayed on a plane or curved surface in an array called 1 D array, 1.5 D array, 1.75 D array, 2 D array, or the like.

The probe 30 may be configured to mechanically move in relation to the subject, and may be a hand-held type probe 30 where the user holds and moves the probe 30. In a case of a photoacoustic microscope, the probe 30 is preferable a focusing probe, with the probe 30 mechanically moving over the surface in relation to the subject. The irradiation position of the irradiation light and the probe 30 preferably move synchronously. An amplifier for amplifying analog signals output from the converting elements 3 may be provided within the probe 30.

Input Unit 12

A mouse, keyboard, touch panel, audio input unit, or the like, may be used as the input unit 12. The input unit 12 is not restricted to being a configuration which the photoacoustic apparatus according to the present embodiment has, and may be provided separately and connected to the photoacoustic apparatus.

Display Unit 8

A liquid crystal display (LCD), cathode ray tube (CRT), organic electroluminescence (EL) display, or the like, may be used as the display unit 8. The display unit 8 is not restricted to being a configuration which the photoacoustic apparatus according to the present embodiment has, and may be provided separately and connected to the photoacoustic apparatus.

Signal Processing Unit 40

A circuit generally called a data acquisition system (DAS) may be sued for the signal collecting unit 9. More specifically, the signal collecting unit 9 includes an amplifier for amplifying received signals, an AD converter for digitizing analog received signals, a first-in-first-out (FIFO) buffer for storing received signals, random access memory (RAM), and other such memory, and so forth.

A central processing unit (CPU), microprocessor unit (MPU), graphics processing unit (GPU), or some other like processor may be used as the first distribution obtaining unit 4 and second distribution obtaining unit 5. A computing circuit such as a field programmable gate array (FPGA) chip or the like may be used as well. The first distribution obtaining unit 4 and second distribution obtaining unit 5 are not restricted to being configured using a single processor or computing circuit, and may be configured using multiple processors or computing circuits.

The first distribution obtaining unit 4 and second distribution obtaining unit 5 may have memory to store reception signals output from the signal collecting unit 9. The memory typically is configured as read only memory (ROM), RAM, a hard disk, and other like storage media. The memory is not restricted to being configured using a single storage medium, and may be configured using multiple storage media.

The display control unit 10, shift unit 7, statistical information obtaining unit 6, region setting unit 13, deciding unit 14, and control unit 11 may also in like manner be configured using one of or a combination of processors such as a CPU or GPU or the like, and circuits such as FPGA chips or the like. These components may also have memory to store reception signals, distribution data, display image data, various types of measurement parameters, and so forth. The memory typically is configured as one or more of read only memory (ROM), RAM, a hard disk, and other like storage media.

Figure 5:
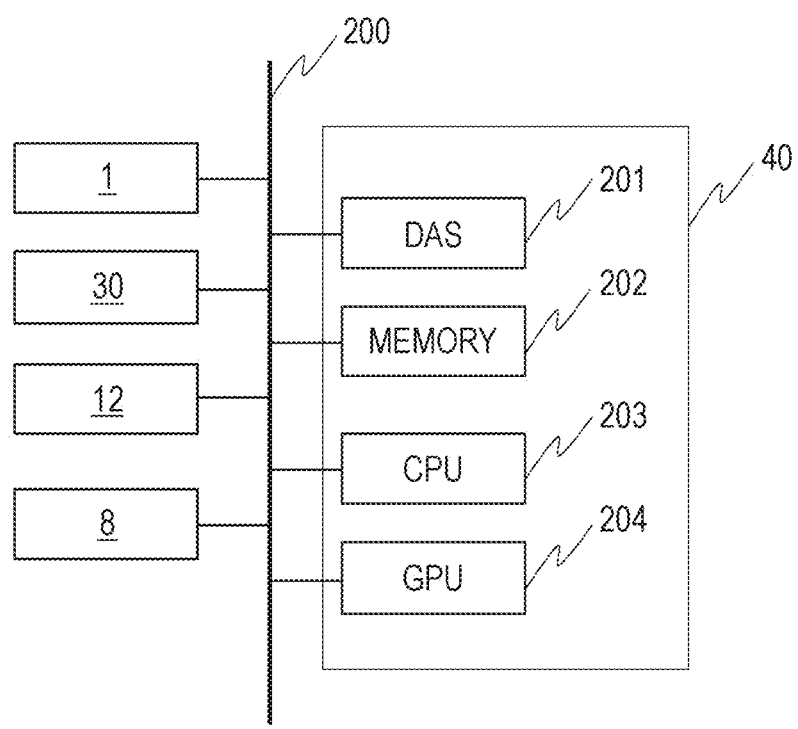
FIG. 5 is a schematic diagram for describing a configuration example of a signal processing unit.

FIG. 5 is a schematic diagram illustrating the relationship between a specific example of the signal processing unit 40 and external devices. In the example in FIG. 5, the signal processing unit 40 includes a DAS 201, memory 202, a CPU 203, and a GPU 204.

The DAS 201 handles a function of the signal collecting unit 9 in the present embodiment. Digital signals transferred from the DAS 201 are stored in the memory 202.

The CPU 203 functions as part of the first distribution obtaining unit 4, second distribution obtaining unit 5, display control unit 10, shift unit 7, statistical information obtaining unit 6, region setting unit 13, deciding unit 14, and control unit 11 according to the present embodiment. Specifically, the CPU 203 accepts various types of parameters and instructions relating to operations from the user via the input unit 12, generates necessary control information, and controls the functional blocks via a system bus 200. The CPU 203 also can perform signal processing such as integration processing and correction processing of digital signals stored in the memory 202. The CPU 203 further writes the digital signals after signal processing into the memory 202 again, to be used for the GPU 204 to generate distribution data.

The GPU 204 functions as part of the first distribution obtaining unit 4, second distribution obtaining unit 5, display control unit 10, shift unit 7, statistical information obtaining unit 6, region setting unit 13, deciding unit 14, and control unit 11 according to the present embodiment. Specifically, the GPU 204 creates distribution data using digital signals that have been subjected to signals processing by the CPU 203 and written to the memory 202. The GPU 204 also can create image data by subjecting the created distribution data to various types of image processing, such as luminance conversion, distortion correction, cropping of target region, and so forth. The CPU 203 is also capable of similar processing.

First Example

A more specific example will be described will be described with reference to FIG. 1. In the present example, the subject is a breast, the subject is irradiated by light across a holding member formed of polymethylpentene which holds the subject, and the probe 30 receives the photoacoustic waves across the holding member. The probe 30 is a 2 D array probe having multiple converting elements in the frequency band of 1 MHz±40%.

First, the subject is irradiated by pulse light from the light source 1 having a wavelength of 797 nm in the present example, and the probe 30 receives the photoacoustic waves. The signal processing unit 40 of the configuration illustrated in FIG. 5 performs image reconfiguration using universal back projection based on the reception signals that have been received. An absorption coefficient distribution is then created using the obtained initial sound pressure distribution, light quantity distribution, and the Grueneisen constant.

The values of the absorption coefficient distribution are in voxel data, each voxel being a cube 0.25 mm in each dimension. The obtained absorption coefficient distribution is 185 voxels deep, 481 voxels wide, and 281 voxels high.

Next, in order to generate positional deviation, the subject is shifted by 1 mm. Thereafter, the subject is irradiated by pulse light from the light source 1 having a wavelength of 756 nm, and the probe 30 receives the photoacoustic waves. The signal processing unit 40 performs image reconfiguration using universal back projection based on the reception signals that have been received. The signal processing unit 40 then creates an absorption coefficient distribution using the obtained initial sound pressure distribution, light quantity distribution, and the Grueneisen constant.

Figure 7:
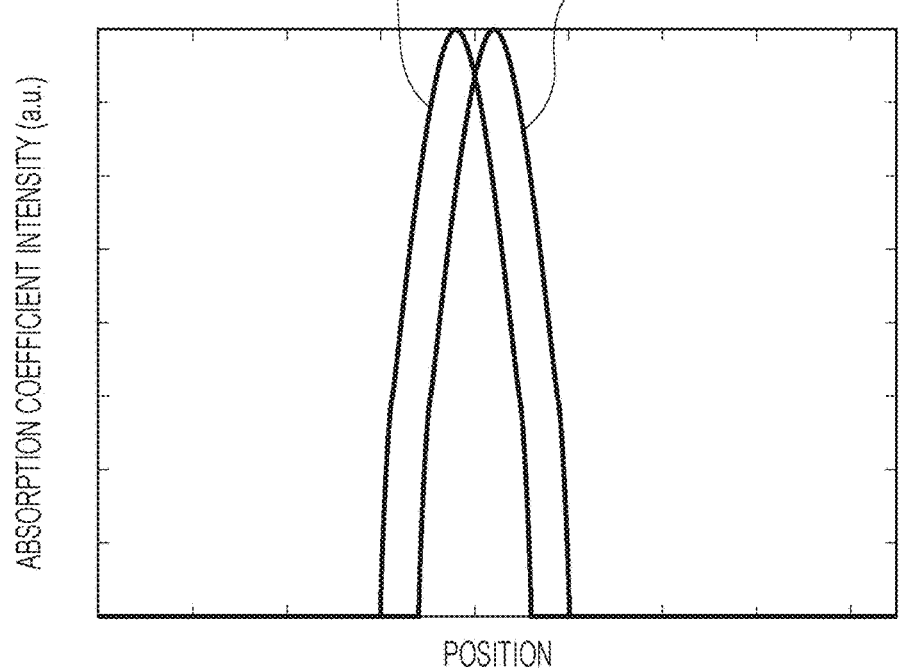
FIG. 7 is a schematic diagram illustrating deviation between a peak within a 756 nm absorption coefficient distribution and a peak within a 797 nm absorption coefficient distribution.

Now, FIG. 7 illustrates the way in which positional deviation occurs among the absorption coefficient distributions between the wavelengths. The peak to the right side in FIG. 7 is the signal intensity at a certain cross-sectional position in the absorption coefficient distribution for 756 nm, and the peak to the left side in FIG. 7 is the signal intensity at the same cross-sectional position in the absorption coefficient distribution for 797 nm. It can be seen from FIG. 7 that the position of the peak to the right is shifted as to the peak at the left.

Figure 8:
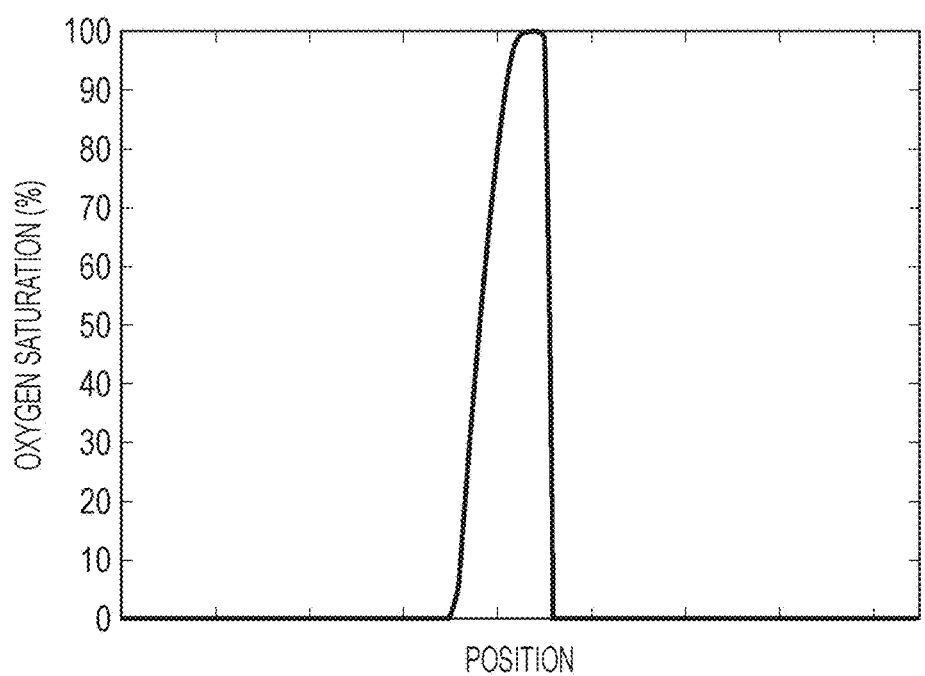
FIG. 8 is a diagram illustrating dispersion within an oxygen saturation distribution in a case where there is positional deviation.
Figure 9:
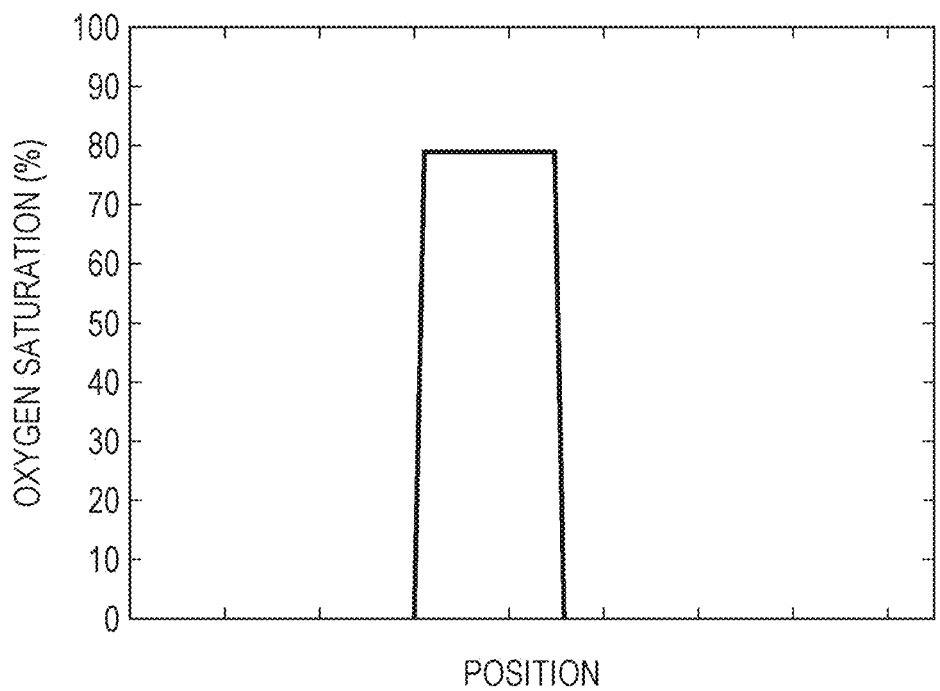
FIG. 9 is a diagram illustrating dispersion within an oxygen saturation distribution in a case where there is no positional deviation.

The signal processing unit 40 calculates the oxygen saturation distribution based on the absorption coefficient distribution for 756 nm and the absorption coefficient distribution for 797 nm. Calculation of the oxygen saturation is performed among corresponding voxels in the different wavelengths, with the oxygen saturation distribution being 185 voxels deep, 481 voxels wide, and 281 voxels high, the same as with the absorption coefficient distributions. A positional deviation state is generated between the subject and the probe, so this oxygen saturation distribution has not been appropriately calculated. FIG. 8 illustrates signal intensity of oxygen saturation at a certain cross-section in the oxygen saturation distribution. The oxygen saturation has not been properly calculated, so it can be seen from FIG. 8 that there is variance in values at the region thought to be corresponding to the blood portion within the oxygen saturation distribution. Assumption will be made that the oxygen saturation distribution is in a range of 0% to 100%. Now, FIG. 9 illustrates an ideal case where there is no positional deviation between absorption coefficient distributions for each wavelength. It can be seen that there is no variance in oxygen saturation in FIG. 9, since the oxygen saturation corresponding to the blood portion of the oxygen saturation distribution has been calculated properly.

Next, upon receiving input from the user, the signal processing unit 40 sets a partial three-dimensional region of the calculated oxygen saturation distribution as a target region. The target region has been set at a portion where intensity is high in the 797 nm initial sound pressure distribution corresponding to the blood portion. An oxygen saturation histogram is calculated in the set target region, and dispersion is calculated from the calculate histogram. The value of dispersion obtained here is high, due to the effects of positional deviation of the subject.

Next, using the 797 nm absorption coefficient distribution as a reference, the target region within the 756 nm absorption coefficient distribution is shifted in parallel one voxel each in the depth, width, and height directions, up to eight voxels. The oxygen saturation distribution within the target region and the dispersion of oxygen saturation distribution are calculated in each of the shifting patterns. The total number of shifting patterns is (8+1+8)×(8+1+8)×(8+1+8)=4,913 patterns, including not shifting.

The shifting pattern of which the dispersion value has the smallest value out of the 4,913 patterns of dispersion values calculated as described above is taken as the vector of the coordinate shifting. The signal processing unit 40 then performs coordinate shifting of the 756 nm absorption coefficient distribution based on the obtained coordinate shift vector, and thus obtains the oxygen saturation distribution. Accordingly, an oxygen saturation distribution regarding which positional deviation correction among waveforms has been corrected can be obtained in the present example. An advantage thereof is that relative positional deviation among many waveforms can be corrected from the initial sound pressure distribution and absorption coefficient distribution obtained at the photoacoustic apparatus, without having to use an ultrasound apparatus, and calculation accuracy of oxygen saturation is improved.

Second Embodiment

Next, a second embodiment will be described. The photoacoustic apparatus according to the present embodiment uses the same device configuration as the photoacoustic apparatus according to the first embodiment, so detailed description of the configurations will be omitted. Note however, there is difference as to the first embodiment with regard to the processing performed by the signal processing unit 40, so description will be made below focusing on differences as to the first embodiment.

A feature of the photoacoustic apparatus according to the present embodiment is that the region setting unit 13 sets the target region automatically. In the steps in FIG. 2, the same processing as in the first embodiment is performed up to S102. In S103 in the present embodiment, the region setting unit 13 first performs masking of the blood vessel portion in the oxygen saturation distribution. The region setting unit 13 sets to 0 the intensity at positions in the oxygen saturation distribution corresponding to positions where the intensity in the absorption coefficient distribution of one wavelength is lower than a predetermined value. The region setting unit 13 then sets at least a partial region that continuous out of the region where the intensity is a predetermined value or higher. Thus, the region setting unit 13 can set the blood vessel portion (portions where intensity in the absorption coefficient distribution is high) as a target region. Initial sound pressure distribution may be used for masking instead of the absorption coefficient distribution.

The processing of S104 and thereafter is the same as in the first embodiment. The region setting unit 13 sets the target region automatically in the present embodiment, based on the intensity in a feature distribution, based on optical absorption in absorption coefficient distribution or the like, so the user is spared this work, and an apparatus with better ease-of-use is provided.

Third Embodiment

Next, a third embodiment will be described. The photoacoustic apparatus according to the present embodiment uses the same device configuration as the photoacoustic apparatus according to the first and second embodiments, so detailed description of the configurations will be omitted. Note however, there is difference as to the first and second embodiments with regard to the processing performed by the signal processing unit 40, so description will be made below focusing on the differences.

A feature of the photoacoustic apparatus according to the present embodiment is that the region setting unit 13 sets multiple target regions at positions different from each other. In the steps in FIG. 2, the same processing as in the first embodiment is performed up to S102. In S103 in the present embodiment, the region setting unit 13 first performs binarization in the oxygen saturation distribution, in the same way as in the second embodiment. Initial sound pressure distribution may be used for binarization instead of the absorption coefficient distribution.

In a case where a region corresponding to the blood vessel portion in the oxygen saturation distribution is large, there is a possibility that positional deviation vectors (positional deviation amount and positional deviation direction) may differ within that region. Accordingly, in the present embodiment, the region setting unit 13 sets multiple target regions in the oxygen saturation distribution obtained by binarization. Note that each target region preferably is in a region corresponding to the blood vessel portion. The size of each target region is a size set in the device beforehand, such as a 20×20 pixel square if two-dimensional, or a 20×20×20 voxel cube if three-dimensional, or the like. The size may be settable by the user.

Thereafter, the processing of S104 and thereafter is applied to each of the multiple target regions. Note that in a case where relative coordinate sift is performed among the absorption coefficient distributions in each target region, there may be discrepancy between the absorption coefficient distribution in one target region and the absorption coefficient distribution in an adjacent target region. This is because there are cases where the positional deviation between the probe 30 and the subject is different in each target region. In this case, the region setting unit 13 preferably sets the target regions so that the target regions have overlapping portions. Alternatively, after ending one target region up to S109, an adjacent target region may be set so that there is no overlapping with the one target region and no discrepancy. That is to say, the flow from setting target regions through deciding positional deviation may be repeated while changing the target regions the processing of S110 and thereafter is the same as in the first and second embodiments.

As described above, the region setting unit 13 according to the present embodiment sets multiple target regions, so positional deviation correction can be performed more accurately. While the region setting unit 13 automatically sets the target regions in the above-described example, an arrangement may be made where the region setting unit 13 sets multiple target regions based on user input, as in the first embodiment.

Fourth Embodiment

Figure 10:
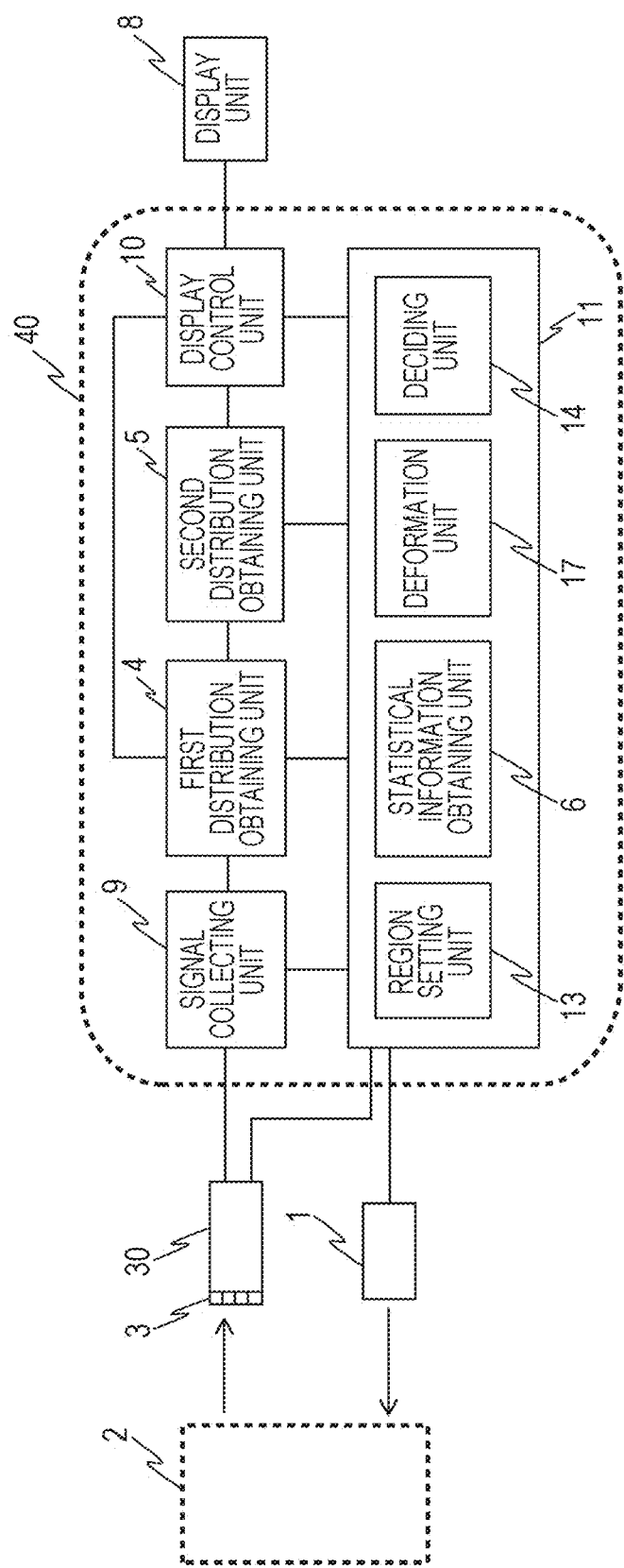
FIG. 10 is a schematic diagram illustrating the configuration of a photoacoustic apparatus according to a fourth embodiment.

Next, a fourth embodiment will be described. The photoacoustic apparatus according to the present embodiment is illustrated in FIG. 10. A deformation unit 17 is a part which differs from the photoacoustic apparatus according to the first through third embodiments. Other than that, the photoacoustic apparatus according to the present embodiment uses the same device configuration as the photoacoustic apparatus according to the first through third embodiments, so detailed description of the configurations will be omitted. Note however, there is difference as to the first through third embodiments with regard to the processing performed by the signal processing unit 40, so description will be made below focusing on the differences.

The photoacoustic apparatus according to the present embodiment is a subject information obtaining apparatus that sets conditions of constraint on the positional deviation among images from multiple images obtained for each wavelength, and performs affine transform, non-rigid transform, and like deformation processing, so that the dispersion value of oxygen saturation is the smallest, thereby performing accurate deformation positioning.

Figure 11:
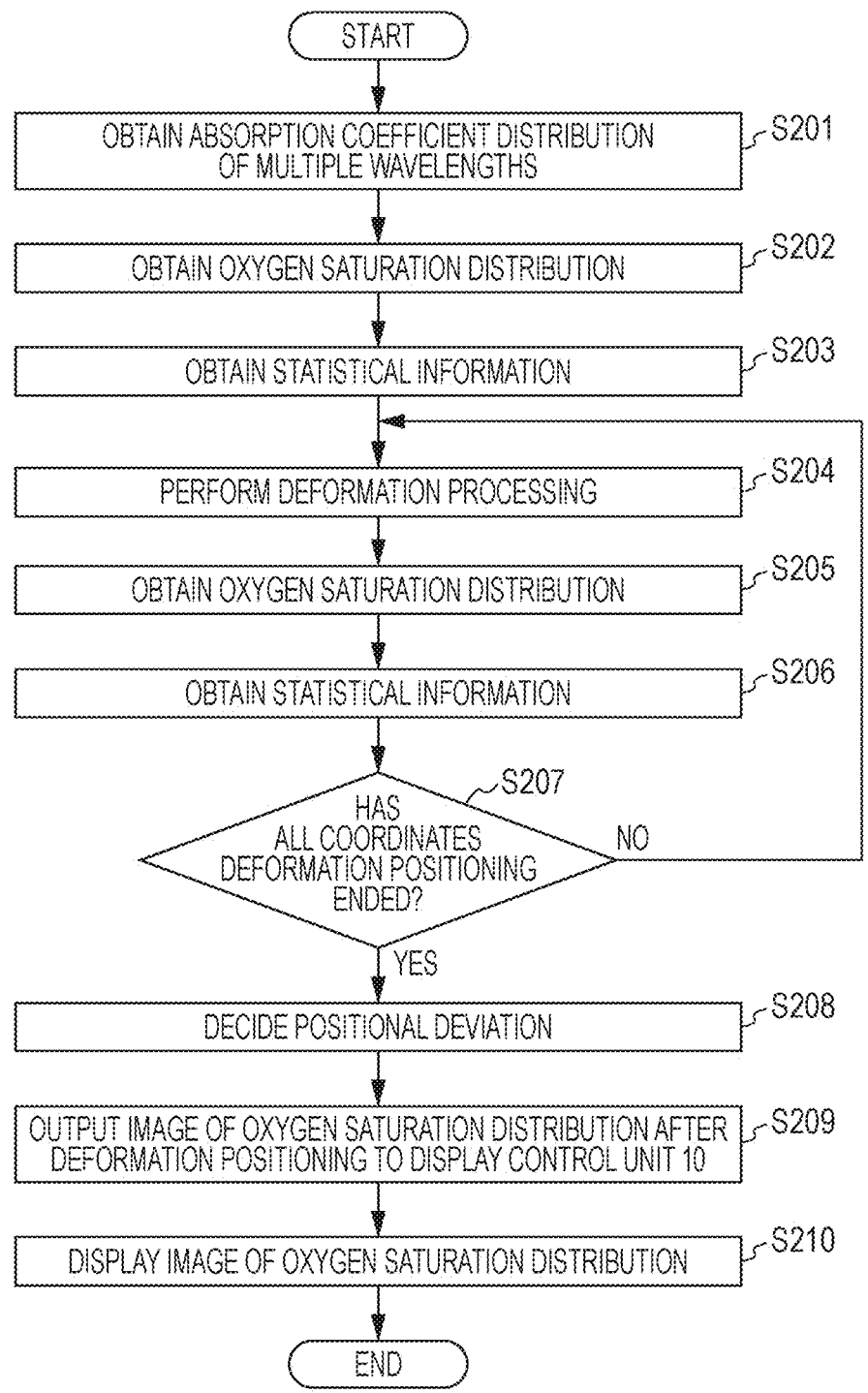
FIG. 11 is a flowchart illustrating operations of the signal processing unit in the fourth embodiment.

An absorption coefficient distribution of the subject is created for each of 756 nm and 797 nm light, in the same way as with the first embodiment. positional deviation correction is performed between the absorption coefficient distributions of the two wavelengths. First, in the steps in FIG. 11, processing the same as in the first embodiment is performed up to S202. In S203 the dispersion value of oxygen saturation is calculated for the entire region of the oxygen saturation distribution in the present embodiment. The oxygen saturation value is weighted according to the intensity of the absorption coefficient distribution at this time.

Thereafter, in S204, the deformation unit 17 performs deformation of the 756 nm absorption coefficient distribution. Known methods based on similarity of luminance information may be used as the method for deformation. For example, grid-like points that correspond between pixels are set on the 756 nm absorption coefficient distribution, and the positions of the corresponding points on the 797 nm absorption coefficient distribution are estimated using similarity of luminance information. This processing may utilize free form deformation (FFD), described in "T.W. Sederberg 'Free Form Deformation of solid geometric models,' Proc. SIGGRAPH '86, vol. 20, no. 4, pp. 151-160, 1986", for example. At this time, the conditional optimization problem which minimizes the cost function E in Expression (7) has to be solved as the evaluation method for deformation positioning.

$$E(I,T) = (1 - ZNCC(I,T)) + \lambda f(I,T) \quad (7)$$

The first term on the right side in Expression (7) is a cost function according to a normalized cross-correlation coefficient, and the second term f(I, T) is sometimes called a constraint term or a penalty term. The second term is a term which applies a constraint to the solution of the normalized cross-correlation cost function of the first term, so as to narrow down to a more suitable solution (regularization term). λ is an optional constant to balance the least square term and the constraint term, and is a value determined by experience. I and T are distribution within the target region of the 756 nm and 797 nm absorption coefficient distributions, respectively. The following Expression (8) yields a normalized cross-correlation (zero mean normalized cross-correlation (ZNCC)).

$$ZNCC(I, T) = \frac{\sum_{k=0}^{N-1} \sum_{j=0}^{M-1} \sum_{i=0}^{L-1} ((I(i,j,k) - \bar{I})(T(i,j,k) - \bar{T}))}{\sqrt{\sum_{k=0}^{N-1} \sum_{j=0}^{M-1} \sum_{i=0}^{L-1} (I(i,j,k) - \bar{I})^2 \times \sum_{k=0}^{N-1} \sum_{j=0}^{M-1} \sum_{i=0}^{L-1} (T(i,j,k) - \bar{T})^2}} \quad (8)$$

Here, L, M, and N are the number of voxels in the depth, width, and height directions of the calculated absorption coefficient distribution, I(i, j, k) is the distribution of the target region in the 756 nm absorption coefficient distribution, $\bar{I}$ is the average value of distribution in the 756 nm target region, T(i, j, k) is the distribution of the target region in the 797 nm absorption coefficient distribution, and $\bar{T}$ is the average value of distribution in the 797 nm target region. This enables calculation of normalized cross-correlation coefficients for I and T. While FFD has been used here as the deforming technique, other interpolation methods may be used, such as radius basis function (RBF) and so forth.

While the normalized cross-correlation coefficient has been used as the cost function, sum of squared distance (SSD), mutual information amount, or the like may be used, as long as a statistical amount representing image similarity, and the statistical amount may be converted so that the images match each other more the smaller the value of the cost function is at this time. The cost function may be calculated for the entire absorption coefficient distribution region, the user may extract a particular region, or a region may be set unique to the apparatus. The entire region of the calculated absorption coefficient distribution is set as the target region here.

The dispersion value of the oxygen saturation was used as the standardization term f(I, T). In this calculation method, oxygen saturation is calculated from the 756 nm absorption coefficient distribution I and 797 nm absorption coefficient distribution T according to Expression (5), and the dispersion of oxygen saturation distribution is calculated. However, there are body tissue portions which do not contain blood, so the oxygen saturation distribution calculated here may be poor in accuracy if the dispersion value of oxygen saturation is calculated for the entire region of the absorption coefficient distribution. This problem can be handled by calculating the dispersion value of the oxygen saturation corresponding to the blood vessel portions, by binarizing portions corresponding to blood vessels when calculating, or weighting the oxygen saturation distribution with the intensity of the absorption coefficient. Here, the oxygen saturation distribution is weighted by the intensity of the absorption coefficient. Also, while Expression (7) has been used as the cost function E, but any format may be used as long as it is an expression with a standardization term such that the variance in oxygen saturation is reduced. At this time, the oxygen saturation distribution is within the range of 0% to 100%, so in a case where the calculated oxygen saturation at the time of performing deformation positioning such that the dispersion value is smallest is not within this range, this is a deformation positioning error. Accordingly, a term may be added as a standardization term so that the calculated oxygen saturation distribution is within this range. Also, a term may be added as a standardization term to suppress change in volume, so that the absorption coefficient distribution is not greatly deformed.

The 756 nm absorption coefficient distribution is deformed by FFD, and in S206 the cost function is calculated between the deformed 756 nm absorption coefficient distribution and the 797 nm absorption coefficient distribution. The 756 nm absorption coefficient distribution is repeatedly deformed to reduce the cost function, and in a case where the cost function is smaller than a threshold value determined beforehand, in S207 the deformation positioning ends since positioning has been sufficiently performed. On the other hand, in a case where the cost function equal to or larger than the threshold value determined beforehand, deformation positioning is performed by repeating the positioning processing. An arrangement may be made for this determination where the number of times that the processing has been repeated is counted, and when the counter value reaches a present number of times, the repeating processing ends at that point. This method is advantageous in that the series of repeating calculations can be expected to end within a certain amount of time, ensuring real-time nature of the entire system. In S208, the deciding unit 14 decides the positional deviation between the probe and subject due to deformation of the subject and so forth, based on the plurality of statistical information calculated in S203 and S206. The amount of deformation where the smallest dispersion is yielded from the multiple dispersions is decided to be the positional deviation between the absorption coefficient distributions here (relative positional deviation between the 756 nm absorption coefficient distribution and 797 nm absorption coefficient distribution). Processing from S209 and thereafter is the same as in the first through third embodiments.

While absorption coefficient distributions of two wavelengths has been used in the present embodiment, the present embodiment is applicable to cases of performing imaging using three or more wavelengths. The object can be achieved here by first performing deformation positioning on the absorption coefficient distribution of two wavelengths using the technique as described above, and thereafter performing deformation positioning between the absorption coefficient distribution regarding which deformation positioning has been completed and the absorption coefficient distribution of another wavelength.

Also, using an absorption coefficient distribution in the present embodiment where the probe is scanned and the absorption coefficient distributions of the pulses are added and averaged, whereby deformation positioning can be performed among the averaged absorption coefficient distributions.

Also, the plurality of distribution data may be subjected to both the coordinate shifting described in the first through third embodiments, and the deformation processing described in the present embodiment. That is to say, at least one of coordinate shifting processing and deformation processing can be executed.

Accordingly, the dispersion of the oxygen saturation is used as a standardization term, thereby correcting positional deviation among the absorption coefficient distributions of multiple waveforms, so that the dispersion value of the oxygen saturation is reduced.

An advantage of the present embodiment is that, if relative positional deviation and deformation is occurring in the initial sound pressure distribution and absorption coefficient distribution among many waveforms, correction can be performed taking into consideration the nature of living tissue, without having to use an ultrasound apparatus. This enables not only parallel movement when correcting positional deviation and deformation, but also more complicated positional deviation and deformation to be corrected. Also, deformation which could not occur in living tissue is not performed during deformation positioning, so good results are obtained regarding calculation accuracy of oxygen saturation.

Fifth Embodiment

Figure 12:
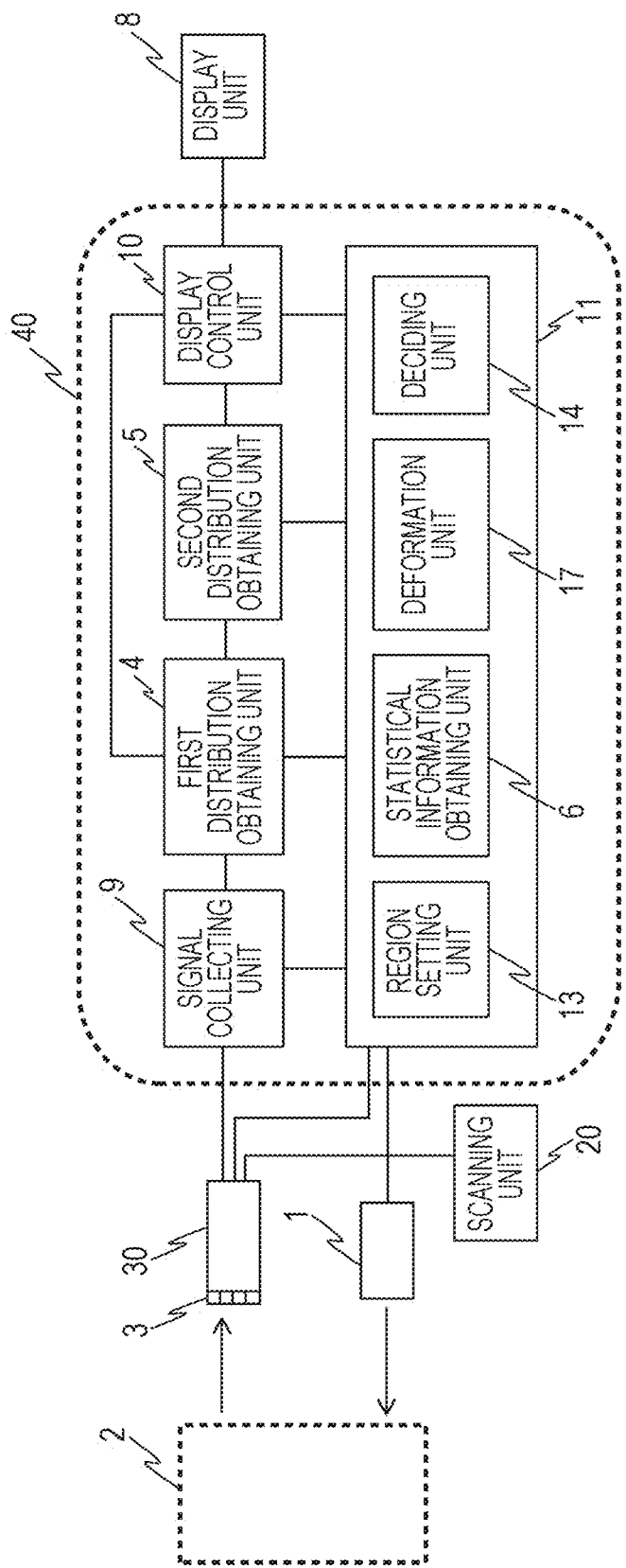
FIG. 12 is a schematic diagram illustrating the configuration of a photoacoustic apparatus according to a fifth embodiment.

Next, a fifth embodiment will be described. The photoacoustic apparatus according to the present embodiment is illustrated in FIG. 12. A scanning unit 20 is a part which differs from the photoacoustic apparatus according to the first through third embodiments. Other than that, the photoacoustic apparatus according to the present embodiment uses the same device configuration, so detailed description of the configurations will be omitted. Note however, there is difference as to the first through fourth embodiments with regard to the processing performed by the signal processing unit 40, so description will be made below focusing on the differences.

In the fifth embodiment, deviation in absorption coefficient distribution occurring due to breathing and body movement at the time of scanning with the probe is corrected at an absorption coefficient distribution calculating unit. Thereafter, deformation positioning is performed to correct the deviation of absorption coefficient distribution wavelengths of pulses as to the generated absorption coefficient distribution, so that the dispersion value of oxygen saturation is the smallest, the method of which will be described. The generated 756 nm absorption coefficient distribution is in a state where absorption coefficient distribution segments for each pulse are positioned by deformation over all scanning positions. By performing deformation positioning of 797 nm absorption coefficient distribution segments as to the 756 nm absorption coefficient distribution, the difference in absorption coefficient values among wavelengths is no larger than if the 756 nm absorption coefficient distribution and 797 nm absorption coefficient distribution are generated independent of each other.

At the time of performing deformation positioning of the 756 nm absorption coefficient distribution and 797 nm absorption coefficient distribution segment, a constriction is set so that the dispersion value of oxygen saturation is small.

The scanning unit 20 scans the light source 1 and probe 30. The light source 1 alone may be scanned, the probe 30 alone may be scanned, both may be scanned independently, and both may be scanned simultaneously.

Figure 13:
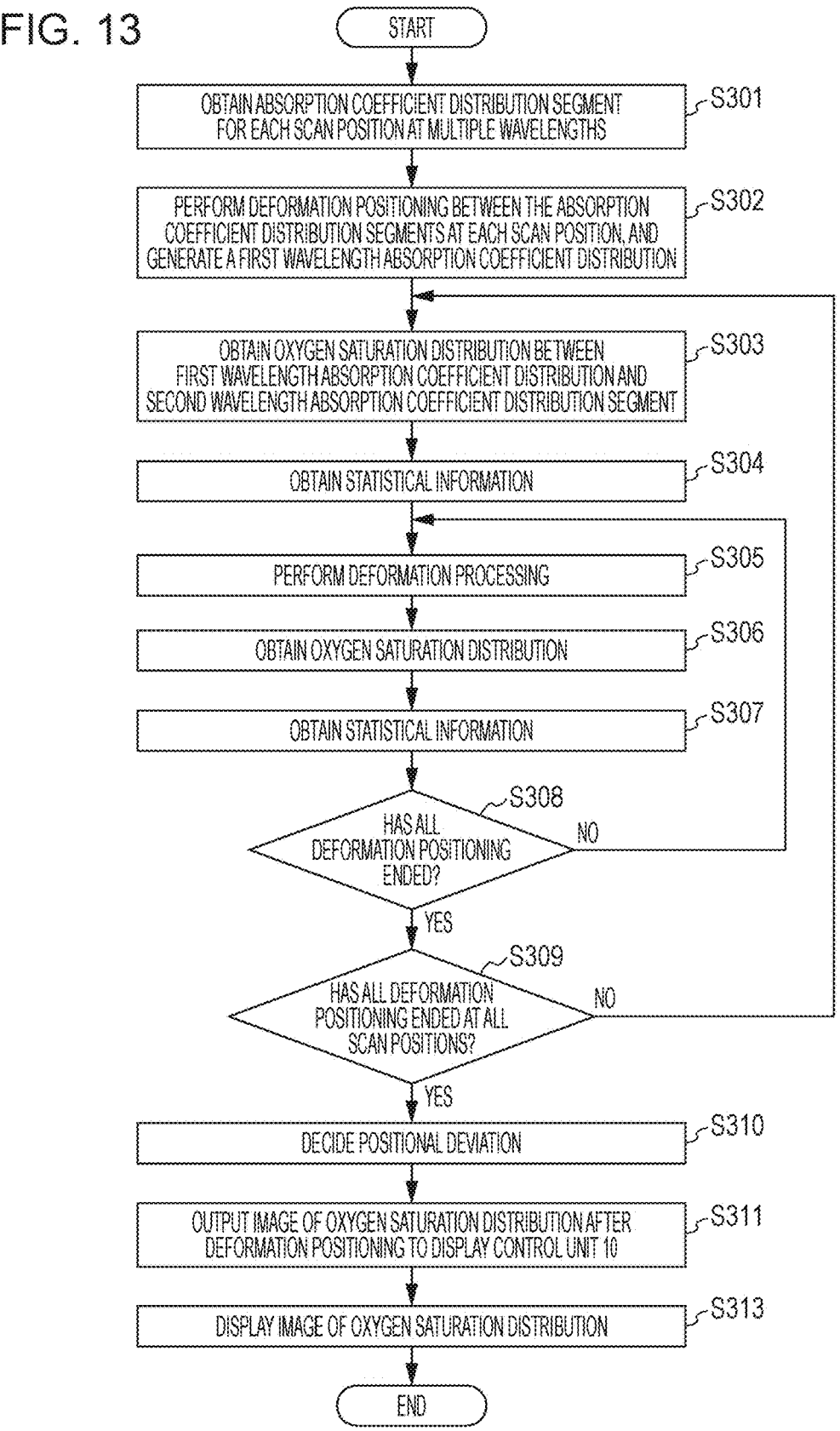
FIG. 13 is a flowchart illustrating operations of the signal processing unit in the fifth embodiment.

In the steps in FIG. 13, first, in S301 the subject is irradiated with pulsed light of both wavelengths 756 nm and 797 nm, and the acoustic waves at a scanning position, which is an acoustic wave probe, are obtained and converted into digital signals. Acoustic waves generated by pulses irradiated at other scanning positions as well are obtained and each converted into digital signals. Image reconstruction is performed for each of the digital signals, and absorption coefficient distribution segments regarding each of the pulses near the scanning position are generated. In the present embodiment, generating of the absorption coefficient distribution segments is performed at once in this step, but the absorption coefficient distribution segments of one wavelength may be performed in parallel during the deformation positioning process from S303 to S309. Next, in S302, due to the scanning rate of the probe, there are places where the absorption coefficient distribution segments regarding the signals obtained by irradiation of the 756 nm wavelength overlap with each other, and from the arithmetic average of the absorption coefficient distribution segments at the scanning positions, one large absorption coefficient distribution can be generated. At the time of generating the one large absorption coefficient distribution, the absorption coefficient distribution segments may be positioned. The size of the absorption coefficient distribution segments corresponding to the pulses preferably is the range where the irradiation light of the pulses is cast, but may be a smaller region than the region where the irradiation light is being cast if deformation positioning of image features such as blood vessels to be positioned can be appropriately performed, or may be the size of the entire absorption coefficient distribution to be generated. In the present embodiment, the size of an absorption coefficient distribution segment is a cubic region 40 mm in each dimension, centered on the irradiation position of each pulse. In a case where the size of the entire absorption coefficient distribution to be generated is to be used as the absorption coefficient distribution segments, deformation positioning is preferably performed using only image features near the pulse scanning position.

Any deformation positioning technique may be used for the deforming positioning method, such as FFD or RBF at the overlapping portions of the absorption coefficient distribution segments. The evaluation function may be any, as long as a statistical amount representing image similarity, such as normalized cross-correlation, mutual information amount, SSD, or the like.

Deformation positioning of the overlapping portion of the absorption coefficient distribution segments is performed here so that the normalized cross-correlation coefficient is largest, and an absorption coefficient distribution is generated for the overlapping portion by arithmetic averaging or the like. Thus, an absorption coefficient distribution corresponding to one wavelength is generated.

Figure 14:
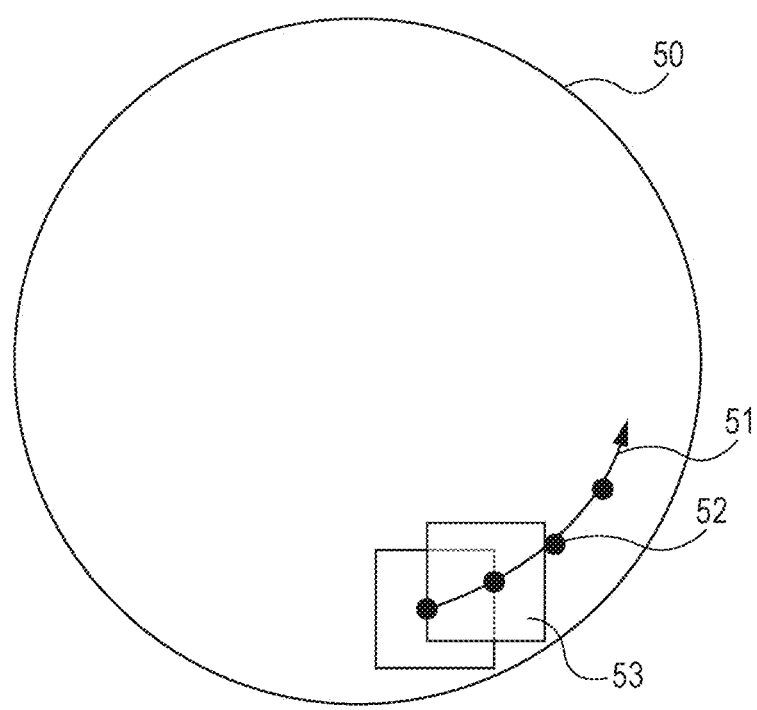
FIG. 14 is a diagram illustrating the way in which imaging is performed in the fifth embodiment.

FIG. 14 illustrates a periphery 50 of the absorption coefficient distribution where absorption coefficient distribution segments of 756 nm wavelength pulses have been integrated, a laser scanning locus 51, irradiation positions 52 of each pulse, and absorption coefficient distribution segments 53 of the pulses. While drawn as a two-dimensional image, there is another dimension in the depth direction of the plane of the drawing, and three-dimensional absorption coefficient distribution segments and absorption coefficient distributions are generated. The absorption coefficient distribution segments 53 of the pulses overall adjacent pulses, with deformation positioning being performed using similarity such as correlation between the overlapping portions.

Next, in the steps of S303 through S309, the integrated 756 nm absorption coefficient distribution that has been generated is subjected to deformation positioning using the dispersion values of oxygen saturation of the absorption coefficient distribution segments at each scanning position in 797 nm. Deformation positioning using the dispersion values of oxygen saturation is performed as follows. First, the integrated 756 nm absorption coefficient distribution and each of the pulse irradiation positions are saved in the first distribution obtaining unit 4. Next, at an absorption coefficient distribution segment corresponding to a certain pulse in 797 nm and the pulse irradiation position thereof, a region corresponding to the absorption coefficient distribution segment corresponding to the certain pulse in 797 nm is cropped out from inside the integrated absorption coefficient distribution of 756 nm. Deformation positioning is performed among the cropped out regions.

At the time of deformation positioning, the dispersion value of the oxygen saturation is made to be smallest using the Expression (7), in the same way as in the fourth embodiment. The dispersion value of the oxygen saturation corresponding to the blood vessel portions can be calculated by binarizing portions corresponding to blood vessels when calculating, or weighting the oxygen saturation distribution with the intensity of the absorption coefficient. Here, the oxygen saturation distribution is weighted by the intensity of the absorption coefficient. Also, Expression (7) has been used as the cost function E, but any format may be used as long as it is an expression with a standardization term such that the variance in oxygen saturation is reduced. Also, a term may be added as a standardization term to suppress change in volume, so that the absorption coefficient distribution is not greatly deformed.

Now, in S307, the 797 nm absorption coefficient distribution is subjected to deformation processing by FFD, and a cost function is calculated between the deformed 797 nm absorption coefficient distribution segments and 756 nm absorption coefficient distribution. In S308, deformation processing of the 756 nm absorption coefficient distribution is repeatedly performed so that the cost function will be small, and if smaller than a threshold value determined beforehand, positioning is deemed to have been performed sufficiently, and deformation positioning is ended. On the other hand, in a case where the cost function equal to or larger than the threshold value determined beforehand, deformation positioning is performed by repeating the positioning processing. An arrangement may be made for this determination where the number of times that the processing has been repeated is counted, and when the counter value reaches a present number of times, the repeating processing ends at that point. This method is advantageous in that the series of repeating calculations can be expected to end within a certain amount of time, ensuring real-time nature of the entire system.

In a case where deformation positioning relating to the absorption coefficient distribution segments has ended in S308, the 797 nm absorption coefficient distribution segment subjected to deformation positioning is held as a part of the 797 nm absorption coefficient distribution, and the steps from S303 to S308 are repeated at the absorption coefficient distribution segment at the next scanning position. In a case where deformation positioning of the 797 nm absorption coefficient distribution segment as to the 756 nm absorption coefficient distribution at the next scanning position has ended, the 797 nm absorption coefficient distribution generated one scanning position earlier is subjected to arithmetic averaging, thereby integrating the absorption coefficient distribution segments.

In a case where deformation positioning of the number of scans to be generated has ended in S309, this state is one where the integrated 756 nm absorption coefficient distribution and the integrated 797 nm absorption coefficient distribution have been generated. Here, the amount of deformation yielding the smallest dispersion of the multiple dispersions is decided to be the positional deviation among the absorption coefficient distributions (relative positional deviation between the absorption coefficient distribution of wavelength $\lambda_1$ and the absorption coefficient distribution of wavelength $\lambda_2$) (S310). Accordingly, comparison computation is performed between the obtained absorption coefficient distributions of the multiple wavelengths, and an image of the oxygen saturation distribution is generated in S311. Processing after S311 is the same as in the first through fourth embodiments.

While absorption coefficient distributions of two wavelengths has been used in the present embodiment, the present embodiment is applicable to cases of performing imaging using three or more wavelengths, in the same way as with the fourth embodiment. The object can be achieved here by first performing deformation positioning on the absorption coefficient distribution of two wavelengths using the technique as described above, and thereafter performing deformation positioning between the absorption coefficient distribution regarding which deformation positioning has been completed and the absorption coefficient distribution of another wavelength.

Performing this deformation positioning enabled deformation positioning to be performed of the 797 nm absorption coefficient distribution as to the 756 nm absorption coefficient distribution of which the deformation had been corrected. Thus, compared with an absorption coefficient distribution obtained by adding the 797 nm wavelength absorption coefficient distribution segments without positioning, and an oxygen saturation distribution calculated among absorption coefficient distributions obtained by adding the 756 nm wavelength absorption coefficient distribution segments without positioning, the deviation among absorption coefficient distribution segments within the wavelength is corrected, and moreover, positional deviation of corresponding absorption coefficient distribution values among different wavelengths is reduced, so the calculation accuracy of oxygen saturation improves.

An advantage of the present embodiment is that, if relative positional deviation and deformation is occurring in generated initial sound pressure distribution and absorption coefficient distribution among many waveforms in a photoacoustic apparatus having a scanning unit, correction of relative positional deviation and deformation can be performed taking into consideration the nature of living tissue, without having to use an ultrasound apparatus. Accordingly, calculation accuracy of the absorption coefficient distribution of one frequency improves in the generated initial sound pressure distribution and absorption coefficient distribution among many waveforms in a photoacoustic apparatus having a scanning unit, and absorption coefficient distribution segments of the other wavelength are matched to this absorption coefficient distribution, which enables not only parallel movement when correcting positional deviation and deformation, but also more complicated positional deviation and deformation to be corrected, and moreover, correction can be performed taking into consideration the nature of living tissue for each pulse. Also, deformation which could not occur in living tissue is not performed during deformation positioning, so good results are obtained regarding calculation accuracy of oxygen saturation.

Other Embodiments

Additional embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2014-122535, filed Jun. 13, 2014, which is hereby incorporated by reference herein in its entirety.

What is claimed is:

1. A photoacoustic apparatus comprising:
   a light source configured to generate a plurality of lights, each of the plurality of lights having a different wavelength from each other;
   a converting element configured to receive photoacoustic waves generated in a subject by irradiating the subject with the plurality of lights;
   a first distribution obtaining unit configured to calculate a plurality of pieces of property distribution information, corresponding to the plurality of lights, which each represents an optical absorption coefficient distribution, an initial sound pressure distribution, or an optical energy absorption density distribution within the subject, the property distribution information being based on photoacoustic waves generated by irradiating the subject with each of the plurality of lights;
   a second distribution obtaining unit configured to calculate, a plurality of times, a plurality of pieces of at least part of oxygen saturation distribution information within the subject by performing at least one of coordinate shifting processing and deformation processing between the plurality of pieces of property distribution information corresponding to the plurality of lights;
   a spatial variance information obtaining unit configured to calculate a plurality of pieces of spatial variance information indicating a spatial variance, corresponding to the plurality of light, in the plurality of pieces of at least part of the oxygen saturation distribution information; and
   a decision unit configured to calculate positional derivation information between the subject and the converting element in a case where the spatial variance indicated by the spatial variance information is smaller than a predetermined value or the smallest from among the plurality of pieces of spatial variance information,
   wherein the second distribution obtaining unit is configured to calculate the oxygen saturation distribution information using the plurality of pieces of the property distribution information after the at least one of the coordinate shifting processing and the deformation processing in according to the positional derivation information.

2. The photoacoustic apparatus according to claim 1,
   wherein the light source is configured to generate the plurality of lights including at least light of a first wavelength and light of a second wavelength that differ from each other,
   wherein the converting element is configured to receive first photoacoustic waves generated in the subject by irradiating the subject with light of the first wavelength and second photoacoustic waves generated in the subject by irradiating the subject with light of the second wavelength,
   wherein the first distribution obtaining unit is configured to:
      obtain first property distribution information which represents an optical absorption coefficient distribution, an initial sound pressure distribution, or an optical energy absorption density distribution corresponding to the first wavelength using first time-sequence reception signals output from the converting element by receiving the first photoacoustic waves, and
      obtain second property distribution information which represents an optical absorption coefficient distribution, an initial sound pressure distribution, or an optical energy absorption density distribution corresponding to the second wavelength using second time-sequence reception signals output from the converting element by receiving the second photoacoustic waves,
      wherein the second distribution obtaining unit is configured to obtain the oxygen saturation distribution information within the subject using the first and second property distribution information.

3. The photoacoustic apparatus according to claim 1, further comprising:
   a region setting unit configured to set a target region in the subject,
      wherein the spatial variance information obtaining unit calculates the spatial variance information of the oxygen saturation distribution information in the target region.

4. The photoacoustic apparatus according to claim 3, wherein the region setting unit sets the target region based on user input.

5. The photoacoustic apparatus according to claim 3, wherein the region setting unit sets the target region based on values of the property distribution information.

6. The photoacoustic apparatus according to claim 3, wherein the region setting unit sets a plurality of pieces of the target regions at different positions in the subject.

7. The photoacoustic apparatus according to claim 1, further comprising:
   a display control unit configured to cause a display unit to display an image of the oxygen saturation distribution information.

8. The photoacoustic apparatus according to claim 1, wherein the spatial variance information obtaining unit obtains a dispersion value as the spatial variance information.

9. A method for processing a signal in a photoacoustic apparatus that includes at least one processor, a light source and a converting element, the method comprising:
   causing the light source to generate a plurality of lights, each of the plurality of lights having a different wavelength from each other;
   receiving, by the converting element, photoacoustic waves generated in a subject by irradiating the subject with the plurality of lights;
   calculating, by the at least one processor, a plurality of pieces of property distribution information, corresponding to the plurality of lights, which each represents an optical absorption coefficient distribution, an initial sound pressure distribution, or optical energy absorption density distribution within the subject, the property distribution information being based on photoacoustic waves generated by irradiating the subject with each of the plurality of lights having a different wavelength from each other;
   calculating, by the at least one processor, a plurality of times, a plurality of pieces of at least part of oxygen saturation distribution information within the subject by performing at least one of coordinate shifting processing and deformation processing between the plurality of the property distributions on optical absorption corresponding to the plurality of lights;

calculating, by the at least one processor, a plurality of pieces of spatial variance information indicating a spatial variance, corresponding to the plurality of light, in the plurality of pieces of at least a part of the oxygen saturation distribution;

calculating, by the at least one processor, positional deviation information between the subject and the converting element configured to receive the photoacoustic waves in a case where the spatial variance indicated by the spatial variance information is smaller than a predetermined value or the smallest from among the plurality of pieces of spatial variance information, and calculating, by the at least one processor, the oxygen saturation distribution information using the plurality of pieces of the property distribution information after the at least one of the coordinate shifting processing and the deformation processing in according to the positional derivation information.

10. A non-transitory computer readable storage medium that stores computer executable instructions to cause a computer having at least one processor to execute a method for processing a signal in a photoacoustic apparatus that includes a light source and a converting element, the method comprising:

causing the light source to generate a plurality of lights, each of the plurality of lights having a different wavelength from each other;

receiving, by the converting element, photoacoustic waves generated in a subject by irradiating the subject with the plurality of lights;

calculating, by the at least one processor, a plurality of pieces of property distribution information, corresponding to the plurality of lights, which each represents an optical absorption coefficient distribution, an initial sound pressure distribution, or optical energy absorption density distribution within the subject, the property distribution information being based on photoacoustic waves generated by irradiating the subject with each of the plurality of lights having a different wavelength from each other;

calculating, by the at least one processor, a plurality of times, a plurality of pieces of at least part of oxygen saturation distribution information within the subject by performing at least one of coordinate shifting processing and deformation processing between the plurality of the property distributions on optical absorption corresponding to the plurality of lights;

calculating, by the at least one processor, a plurality of pieces of spatial variance information indicating a spatial variance, corresponding to the plurality of light, in the plurality of pieces of at least a part of the oxygen saturation distribution;

calculating, by the at least one processor, positional deviation information between the subject and the converting element configured to receive the photoacoustic waves in a case where the spatial variance indicated by the spatial variance information is smaller than a predetermined value or the smallest from among the plurality of pieces of spatial variance information; and calculating, by the at least one processor, the oxygen saturation distribution information using the plurality of pieces of the property distribution information after the at least one of the coordinate shifting processing and the deformation processing in according to the positional derivation information.

* * * * *